United States Patent
Berna Tejero et al.

(10) Patent No.: US 8,237,001 B2
(45) Date of Patent: *Aug. 7, 2012

(54) PROCESS FOR OBTENTION OF HIGHLY-LINEAL, ADJUSTABLE-ISOMERY MONOALKYLATED AROMATIC COMPOUNDS

(75) Inventors: José Luis Berna Tejero, Boadilla del Monte (ES); José Luis Goncalvez De Almeida, Algecira (ES)

(73) Assignee: Cepsa Quimica, S.A., Madrid (ES)

( * ) Notice: Subject to any disclaimer, the term of this patent is extended or adjusted under 35 U.S.C. 154(b) by 52 days.

This patent is subject to a terminal disclaimer.

(21) Appl. No.: 12/746,485

(22) PCT Filed: Dec. 4, 2007

(86) PCT No.: PCT/ES2007/000711
§ 371 (c)(1),
(2), (4) Date: Aug. 17, 2010

(87) PCT Pub. No.: WO2009/071709
PCT Pub. Date: Jun. 11, 2009

(65) Prior Publication Data
US 2010/0305373 A1    Dec. 2, 2010

(51) Int. Cl.
*C07C 2/66*    (2006.01)
(52) U.S. Cl. .......................... 585/449; 585/455; 585/467
(58) Field of Classification Search .................. 585/449, 585/455, 467
See application file for complete search history.

(56) References Cited

U.S. PATENT DOCUMENTS

| | | |
|---|---|---|
| 5,146,026 A | 9/1992 | Berna Tejero et al. |
| 5,276,231 A | 1/1994 | Kocal et al. |
| 2003/0166481 A1 | 9/2003 | Smith et al. |
| 2009/0221464 A1 | 9/2009 | Berna Tejero et al. |

FOREIGN PATENT DOCUMENTS

| | | |
|---|---|---|
| ES | 2 007 545 | 6/1989 |
| WO | WO 2006/108883 | 10/2006 |
| WO | WO 2007/104805 | 9/2007 |

OTHER PUBLICATIONS

Berna et al. "The Fate of LAS in the Environment." *Tenside Surfactants Detergents* vol. 26. (1989) pp. 101-107.
Cavalli et al. "Iso-Branching of LAS Biodegradation Study of Two Model Compounds." *Toxicological and Environmental Chemistry*, vol. 54. (1995) pp. 167-186.
Edited by Falbe, J. "Surfactants in Consumer Products: Theory, Technology, and Application." *Springer Verlag* New York (1987) pp. 4-15.
Nielsen et al. "Environmental fate of commercial LAS. An Overview on the fate of the Iso-branched and Dialyltetralin co-products." *The Cler Review*, vol. 2, No. 1 (1996) pp. 14-27.
Shah, B.R. "UOP HF Alkylation Process.—Handbook of Petroleum Refining Process" *Robert A. Mayers.* (1986) pp. I-3-I-21.
Thomas et al. "Towards a Green Synthesis of LAB's: Effect of Rare Earth Metal Ions on the Benzone Alkylation with 1-Dodecene over NaFAU-Y Zeolites." *J. Mater Sci.* vol. 41. 2006. pp. 1611-1616.

*Primary Examiner* — Thuan Dinh Dang
(74) *Attorney, Agent, or Firm* — Merchant & Gould P.C.

(57) ABSTRACT

The present invention refers to a procedure for obtaining a linear monoalkylaromatic compound, with adjustable 2-phenyl isomer content and an extremely low sulphonation color, in which a catalytic system is used based on highly stable and active solid catalysts and with a high selectivity for linear monoalkylaromatic compounds.

21 Claims, 3 Drawing Sheets

PROCESS FOR OBTENTION OF HIGHLY-LINEAL, ADJUSTABLE-ISOMERY MONOALKYLATED AROMATIC COMPOUNDS

This application is a National Stage Application of PCT/ES2007/000711, filed 4 Dec. 2007, and which application is incorporated herein by reference. To the extent appropriate, a claim of priority is made to the above disclosed application.

FIELD OF THE INVENTION

The present invention refers in general to the catalytic alkylation reactions of aromatic compounds and in particular to the zeolite type catalysts to used in these reactions.

STATE OF THE ART

Alkyl aromatic compounds are an important family of substances that are used as raw materials in numerous industrial fields, such as that of plasticizers, polymeric materials, insecticides, in agriculture to prevent the agglomeration of fertilizers, in the manufacture of textiles and fibres, in the leather and hides industry, herbicides, industrial cleaning processes, in the photography industry, in the manufacture of adhesives and in firefighting products such as humidifying agents, in electrochemical processes for the removal of dirt and greases from the surface of a substrate, and in biodegradable detergents, this being the case of the linear mono-alkyl aromatic compounds (*Surfactants in Consumers Products, Theory, Technology, and Application*, Edited by J. Falbe, Springer Verlag, 1987).

The standard process used by the petrochemical industry for producing linear mono-alkyl aromatic compounds, especially for applications in detergents, consists of dehydrogenating linear paraffins in order to obtain linear mono-olefins, and then to carry out the alkylation of the benzene with these mono-olefins so as to form the linear chain mono-alkylated product (linear mono-alkyl aromatic), also referred to as Linear Alkylbenzene (LAB). Linear Alkylsulphonate (LAS) is the product that is used in the end detergent formulations. This LAS is produced by sulphonation of the LAB and subsequent neutralization of the corresponding Sulphonic Acids (HLAS) with aqueous solutions of alkaline or alkaline-earth hydroxides, according to standard state-of-the-art procedures. The linear olefins used in the process have between nine and sixteen carbon atoms. The alkylation step occurs in the liquid phase, in the presence of Friedel-Craft type catalysts, for instance, hydrofluoric acid. The HF process is well known and used commercially (it produces around 75% of the 3.3 million metric tons of LAB produced a year), producing a high yield (>92% by weight) in LAB with a relatively low selectivity towards 2-phenyl isomers, of less than 20%. The integrated process for LAB production is described in *Handbook of Petroleum Refining Process*, published by Robert A. Meyers, to 1986, p. 1-23, which is adjoined as a reference. U.S. Pat. No. 5,276,231 describes the intermediate steps of the LAB production process, such as selective hydrogenation of the diolefin by-products formed in the dehydrogenation of paraffins and the separation of non-linear by-products from the dehydrogenation step stream. The use of HF, however, presents some drawbacks at operational level, as it requires very careful handling and equipment made with special materials due to its high corrosive capacity, which is translated into higher fixed and operating costs, so attempts have been made to develop alternative catalysts based on solids of an acid nature. At present, the only process implemented at industrial level using heterogeneous catalysis is the DETAL® process (based on patents PI 9204326-7, ES 2 007 545 and U.S. Pat. No. 5,146,026), which produces around 15% of the world output of LAB. It is characterized by using amorphous fluoridated aluminosilicates as a heterogeneous catalyst, and it produces around 30% by weight of 2-phenyl isomers.

The alkylation reaction may be characterized with the following indices: conversion, selectivity towards mono-alkylbenzene and isomer distribution:

i) Alkylation conversion or, more specifically, fractional conversion: In the alkylation reaction considered in this invention, the aromatic is always used in stoichiometric excess in relation to the olefins. The fractional conversion may be defined as the fraction of the limiting reagent, in this case olefin, which is consumed to generate all the products, thus:

$$\text{Conversion} = \frac{N_{A0} - N_A}{N_{A0}} * 100$$

where $N_{A0}$ is the number of olefin moles at the input of the reactor and $N_A$ is the moles of the same reagent at the output of the reactor.

ii) Selectivity towards mono-alkylaromatics: It is defined as $$Sel_{mono-alquilbenceno} = \frac{W_{mono-alquilbenceno}}{W_{ligeros} + W_{mono-alquilbenceno} + W_{Alquilatopesadoo}} * 100$$

W mono-alkylbenzene

Sel mono-alkylbenzene W lights W mono-alkylbenzene W heavy alkylate
where $W_{mono-alkylate}$ is the weight of the mono-alkylated aromatic compound (mono-alkylaromatic) of interest produced, $W_{lights}$ is the weight of all the by-products lighter than the lightest mono-alkylaromatic of interest, and $W_{heavy\ alkylate}$ is the total weight of those species whose molecular weights are higher than those of the mono-alkylaromatic compounds produced.

The heavy alkylate group comprises all the chemical species with molecular weights higher than the mono-alkylaromatic compound. It is usually composed of poly-alkylaromatics (mainly di-alkylaromatics), diphenyl alkanes, oligomerized olefins and alkylates of these oligomerized olefins formed during the alkylation step. These products are mainly generated during the alkylation reaction. The di-alkylaromatics are generated by alkylation of a previously formed mono-alkylaromatic with an olefin. The di-phenylalkanes are formed by alkylation of the benzene with a diolefin which has been dehydrocyclized. Formation of heavy by-products of this kind in the process of obtaining mono-alkylaromatic compound is wanted, as these by-products have no detersive power (detergent capacity) in the washing process on account of their high lipophilic nature. On being formed, they reduce the economic yield of the process for obtaining mono-alkylaromatic compound through not making integral utilization of the raw materials. In addition, they have to be separated from the mono-alkylaromatic compound so as not to affect so as not to affect the surfactant power of the end LAS, and they are marketed as lower value-added emulsifiers. In addition, within the heavy alkylate there are other compounds to be taken into account, such as the alkyl-polyaromatics, generated by alkylation with mono-olefins of polyaromatic compounds generated in the dehydrogenation step. Even at trace level, these by-products drastically lower the quality of the end LAS, as they increase its sulphonation colour considerably. Furthermore, they cannot be separated from the product of interest as they appear at trace level and elute together with the heaviest mono-alkylated LAB due to overlapping of their distillation temperature ranges.

iii) Isomer distribution: Amongst the mono-alkylaromatics produced, the isomer distribution may be defined as the percentage by weight of each type of isomer produced, such as 2-phenyl, 3-phenyl . . . 6-phenyl isomers, as well as the branched alkylate.

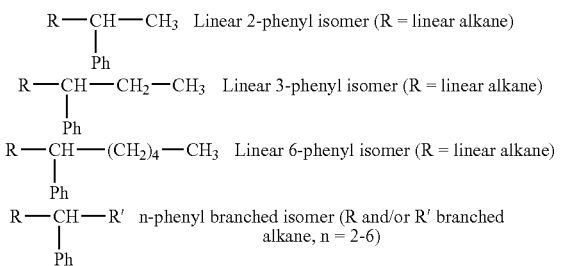

Isomer distribution plays a very important role in the solubility and stability of the end detergents, especially liquid formulations, as well as in their surface activity and in their biodegradation rate.

2-phenyl isomers are those alkylated molecules that have the aromatic rink linked to the alkyl chain in position 2 of the alkylic chain. 2-phenyl isomer content is defined as the percentage by weight of the 2-phenyl isomer in a mixture of LAB or LAS, and it is calculated from the following formula:

2-phenyl isomer [%]=(weight of 2-phenyl isomer)*100/(total weight of LAB or LAS)

Today, the technologies implemented at industrial level (HF and DETAL®) only enable LAB to be produced with average contents (18 and 30%, respectively) of 2-phenyl isomers. in terms of solubility and stability, the ideal range of 2-phenyl isomer concentration is between 25-30% by weight. LAB mixtures, however, with an external isomer content (2+3 phenyl) of more than 60% by weight are characterized by providing a LAS with highly enhanced surface activity, after sulphonation and neutralization. These LAS, however, present a significant drawback caused by their low solubility in cold water and high viscosity. LAS mixtures comprising more than 60% by weight of external isomers (2+3 phenyl) tend to form highly insoluble gels (low cooling cloud temperature) with a high viscosity, which makes them hard to handle and process. This is the reason why it would be desirable to include a hydrotrope in order to improve the solubility of the end surfactant when the content of 2-phenyl isomer is above 60% by weight. Although there are many patents connected with the use of hydrotopes, one of them is considered as the most recommendable for this process. PCT/ES2005000169 refers to a process for obtaining a suitable hydrotrope from previously dehydrogenated paraffins, specifically from those by-products extracted during the mono-olefin purification step.

Finally, branched alkylaromatic compounds (branched alkylates) may be defined as those of the alkylaromatic compounds in which the alkylic chain bonding with the aromatic ring is not a linear or normal alkyl group, but a branched one. These non-normal alkyl groups have radicals such as methyl, ethyl, propyl, isopropyl, butyl, isobutyl, terc-butyl, and different variants of hexyl, heptyl, octyl bonded anywhere on the alkyl chain except at the ends of the chain. Branched alkylates are generated by alkylation with the branched olefins derived from those branched paraffins that are present in the fresh starting paraffins, or by alkylic transposition processes which occur during the dehydrogenation and alkylation steps.

Amongst the branched alkylates, there are alkylates that have one of the aliphatic alkyl group carbon atoms in a quaternary carbon position. The quaternary carbon atom in the alkyl chain is defined as a carbon that is linked to four other carbon atoms and one of these may be bonded to a carbon atom in the phenyl group, forming a quaternary alkyl-phenylalkane. If the quaternary carbon is the second carbon atom in the alkyl chain, the quaternary carbon present in the resultant 2-alkyl-2-phenylalkane may be called "terminal quaternary carbon". We know that, just like the single branched alkylates, this species has a biodegradation rate similar to linear alkylbenzene sulphonate. However, when the quaternary carbon is another alkyl chain carbon atom, 5-methyl, 5-phenylalkane for instance, it is referred to as "internal quaternary carbon", and the corresponding alkylbenzene sulphonate has a much slower biodegradation rate. The articles entitled "*Iso-branching of LAS biodegradation study of two model compounds*", L. Cavalli, G. Cassani, M. Lazzarin, C. Maraschin, G. Nuzzi, J. L. Berna, J. Bravo, J. Ferrer, A. Masno, Toxicology & Environmental Chemistry. Vol. 54, pag. 167-186, 1966 and "*Biodegradation of co-products of commercial LAS*", A. M. Nielsen, L. N. Britton, L. Cavalli, J. L. Berna, The Cler Review, Vol. 2, No1, pag.14-27 (1996), provide scientific evidence of the biodegradation behaviour of these branched alkylbenzene derivatives.

The international patent application WO2007/104805, considered as the prior art for this invention, refers to a procedure for obtaining linear alkylbenzene sulphonates with an adjustable 2-phenyl isomer content and an extremely low sulphonation colour, in which use is made of a catalytic system based on solid highly stable catalysts with a high selectivity towards mono-alkylate compounds. However, by means of the procedure described in this patent substantial branched alkylbenzene contents are produced (more to than 4% by weight, although as much as 10% by weight may be attained in certain operating conditions), considerably higher than those produced both in the standard industrial process based on homogeneous catalysis with HF (around 3.5% en peso) and in the industrial process based on heterogeneous catalysis (DETAL® process, which produces around 3% by weight of these branched products). Since the rapid and complete biodegradability of the LAS derived from both industrial processes has been shown for those branched alkylate contents (Berna, J. L. et al, Tenside Surfactants Detergents 26 (1989), 2), it would be recommendable for the new alkylation processes based on heterogeneous catalysis to be able to generate linear mono-alkylaromatic compounds with preferably lower, or at least similar, amounts of these branched by-products than those of the technologies currently in use. In this way, an optimum environmental behaviour of the sulphonated and neutralized end product (LAS) is assured.

Furthermore, although the catalysts envisaged in international patent application WO2007/104805 enable the duration of the reaction cycles to be increased compared with the heterogeneous catalysts currently used in the DETAL process (60 hours versus 24 hours with current heterogeneous technology), at industrial level it is important to be able to increase this duration even more. In this way, the frequency and number of catalyst washing cycles may be reduced. This is reflected in a lowering of the operating costs of the facility (longer net reactor operating time and reduction in the costs entailed in the catalyst regeneration step), as well as reduced energy consumption (regeneration agent pumping and heating) and pollutant emissions associated with this process.

Lastly, although the catalysts envisaged in international patent application WO2007/104805 enable the formation of heavy by-products to be reduced, compared with existing technology, it would be advantageous to be able to reduce their generation even more so as to maximize the economic efficiency of the LAB production process (integral utilization of the raw materials), as well as improving the quality of the product by means of a reduction in its sulphonation colour,

DESCRIPTION OF THE INVENTION

The present invention provides a procedure for obtaining mono-alkylaromatic compounds with high linearity (they will be called linear mono-alkylaromatics although they may contain minimal amounts of branched alkylate), a minimal heavy alkylate content, and a minimal colour, while also having adjustable 2-phenyl isomer contents, which uses a new low 2-phenyl catalyst that can be more selective, active and stable than those envisaged in the prior art. Owing to its greater selectivity towards the mono-alkylaromatic compounds, this new catalyst can produce an end product with a heavy alkylate content lower than that provided by the prior art, which increases the economic efficiency of the process through raising the utilization of the raw materials, while at the same time upgrading its quality due to the reduction of the sulphonation colour of the resultant LAS. This colour is further minimized by means of a suitable purification both of the raw materials and of the resultant linear mono-alkylaromatic compound. In addition, a linear mono-alkylaromatic compound is obtained with a branched alkylate content equivalent to that of the technologies in use in the sector, which assures a quick full biodegradation of the resultant LAS. The catalyst is more stable against de-activation than those contemplated in the prior art, which provides for longer reaction cycles and less frequent washing cycles, while at the same time a higher activity is maintained, which results in lower operating costs.

This procedure includes a process of utilization of the impurities of the intermediate currents so as to generate a hydrotrope that, added appropriately when the 2-phenyl isomer content in the mono-alkylaromatic compound is over 60% by weight, enables a product to be obtained with a higher solubility than when adding other hydrotropes customary in the prior art. In addition, as the new catalyst is more stable against soiling de-activation, the duration of the reaction cycles is successfully increased and the frequency of the washing cycles reduced. This result in longer production cycles and a reduction in the energy consumption levels associated with the washing regeneration step (washing agent pumping and heating).

A first aspect of the invention, therefore, refers to a procedure for obtaining a linear mono-alkylaromatic compound with a 2-phenyl isomer content of between 18-70% by weight by means of the catalytic alkylation of an aromatic compound with a purified alkylizing agent comprising the following steps:
i) dehydrogenating a supply of linear paraffins catalytically, producing linear mono-olefins, unconverted paraffins and a certain quantity of by-products such as diolefins and non-linear compounds.
ii) treating the effluent of step i) in order to hydrogenate selectively the diolefins produced as a by-product at step i) to mono-olefins, thereby obtaining a raw alkylation agent comprising linear mono-olefins, unconverted paraffins and non-linear compounds.
iii) purifying the raw alkylation agent by separating the non-linear products contained in the step ii) effluent, so that a purified alkylation agent is obtained composed of mono-olefins and paraffins.
iv) treating the non-linear products extracted in step iii) to form the hydrotropic precursor.
v) alkylating the aromatic hydrocarbon with the mono-olefins present in the purified alkylation agent, by means of combining two alkylation processes based on:
a) an alkylation process with a catalyst that produces a linear alkylaromatic compound with a maximum 2-phenyl isomer content of 20% by weight
b) an alkylation process with a catalyst that produces a linear alkylaromatic compound with a minimum 2-phenyl isomer content of 20% by weight, which comprises a MOR typezeolite, between 0.01%-0.20% by weight of at least one of the selected metals of the group consisting of: Li, Na, K, Mg or Ca with a maximum of 0.01% of Na, and between 0-0.5% by weight of at least one of the selected metals of the group consisting of Ti, Zr, Hf
vi) fractionating the step v) effluent in order to separate the aromatic compounds that have not reacted, the paraffins and the heaviest by-products of the linear mono-alkylaromatic compounds of interest.
vii) purifying the fraction of linear mono-alkylaromatic compounds of interest that comes from step vi)

This process is characterized in that the catalyst, which can produce a maximum of 20% by weight 2-phenyl isomers, comprises a FAU-type zeolite, between 0.5%-2% by weight, of at least one of the selected metals of the group consisting of: Li, Na, K, Mg or Ca and between 8%-16.5% by weight of at least one of the selected rare earth metals of the group consisting of La, Ce, Pr, Nd, Pm, Sm or Eu;

In this invention, when we talk of FAU or EMT-FAU type zeolites, we are referring to the group of zeolites with isotypic structures corresponding to the FAU structural type, such as: Y zeolite, Na—X zeolite, siliceous Na—Y, Linde X zeolite, Linde Y zeolite, ZSM-3 zeolite and ZSM-20 zeolite, preferably a Linde zeolite or a Y zeolite.

In the present invention when we talk of MOR type zeolites, we refer to the group of zeolites with isotypical structures corresponding to the MOR structural MOR type, such as: mordenite, Na-D zeolite and Ca-Q zeolite, most preferably to mordenite.

In the particular embodiment of the present invention the catalyst that produces a maximum of 20% of 2-phenyl isomers comprises a quantity of 0.9% by weight of Na.

In another particular embodiment of the present invention the catalyst that produces a maximum of 20% of 2-phenyl isomers comprises between 4.5-10% by weight of La, between 1.2-4% by weight of Ce, between 0.5-1.5% by weight of Pr and between 2-3% by weight of Nd.

In another particular embodiment of the present invention the catalyst that produces a maximum of 20% 2-phenyl isomers comprises:
a) a powder X-ray diffraction pattern characterized in that the most intense diffraction peak appears at the angle 2 theta corresponding to 6.2°, and the other main peaks at the diffraction angles 2 theta corresponding to 23.6°, 20.3°, 21.6°, 27.0°, 31.3°, arranged in descending order of intensity of the associated peaks
b) a total silicon/aluminium molar ratio between 0.5:1.0 and 3.0:1.0, preferably between 0.5:1.0 and 2.0:1.0
c) a structural network silicon/aluminium molar ratio between 1.5:1.0 and 2.5:1.0, preferably between 2.1:1.0 and 2.3:1.0
d) a total specific area (BET) comprised between 500-1000 m$^2$/g, preferably between 600 and 700 m2/g
e) a micropore area comprised between 500-900 m$^2$/g, preferably between 500 and 600 m2 f) a specific micropore volume comprised between 0.1-0.3 ml/g, preferably between 0.19 and 0.22 ml/g g) a macropore distribution where the macropore diameter is in the range comprised between 20-2000 angstroms, preferably 40 angstroms In a particular embodiment of the present invention, the step i) paraffins comprise straight chain alkanes comprising between 8-30 carbon atoms, preferably between 10-16 carbon atoms, more preferably they comprise between 10-14 carbon atoms. These paraffins may be dehydrogenated and purified by means of any process described in the prior art.

In a particular embodiment of the present invention, the aromatic hydrocarbon is the selected aromatic hydrocarbon of the group: toluene, xylene, benzene or mixtures of same, but preferably benzene.

In a particular embodiment of the present invention, the aromatic hydrocarbon and the olefins are mixed prior to the step v) alkylation reaction in an aromatic hydrocarbon:olefin molar ratio comprised between 5:1-70:1, preferably between 10:1-30:1, but more preferably between 10:1-15:1.

In a particular embodiment of the present invention, the mixture of the aromatic hydrocarbon and the purified alkylation agent comprises a maximum of 0.3% by weight of non-linear compounds.

In a particular embodiment of the present invention, the mixture of the aromatic hydrocarbon and the purified alkylation agent also comprises between 0-0.1% by weight of water.

In a particular embodiment of the present invention, the step v) alkylation reactions are carried out simultaneously.

In a particular embodiment of the present invention, the step v) alkylation reaction is carried out in a reactor with a catalyst arrangement selected from the group consisting of: a fixed bed with a single catalyst, a fixed bed with two different catalysts, completely mixed, at least two different fixed beds each with the same catalyst, at least two different fixed beds each with a different catalyst, a fluidized bed with one or more different catalysts, a slurry reactor with one or more different catalysts.

In a particular embodiment of the present invention the step v) alkylation reaction is carried out in a reactor configuration which comprises at least one of the reactor configurations selected from the group consisting of: an independent reactor, at least two parallel reactors, at least two series reactors and combinations of these configurations.

In a particular embodiment of the present invention, the step iii) raw alkylation agent purification process is carried out by means of non-linear impurity separation techniques familiar to an expert on the matter, such as for example, hydrogenation, fractioning and selective adsorption. In the case of selective adsorption, the adsorbent bed is composed of at least one of the materials selected from the group consisting of: zeolites, silica, silica gel, macroporous magnesium silicate, activated alumina, silica-alumina, clays, molecular sieves, cellulose acetate, macroporous polystyrene gel, activated carbon and organoselective polymeric membranes.

In a particular embodiment of the present invention, the treatment for forming the hydrotropic precursor in step iv) comprises:

a) fractionating the non-linear compounds obtained at step ii) by means of distillation at atmospheric pressure, the distillation range of the fraction of interest being that comprised between 195° C. and 259° C.

b) hydrogenating selectively the poly-aromatic species contained in the fraction of interest distilled in the previous step.

In a particular embodiment of the present invention, the hydrotropic precursor obtained in step iv) comprises:

2 to 20% by weight of alkylaromatic compounds with one or more alkyl groups, which have a total of 4 carbon atoms.

5 to 40% by weight of alkylaromatic compounds with one or more alkyl groups, which have a total of 5 carbon atoms.

to 30% by weight of alkylaromatic compounds with one or more alkyl groups, which have a total of 6 carbon atoms.

0.5 to 50% by weight of alkylaromatic compounds with one or more alkyl groups, which have a total of 7 carbon atoms.

0.01 to 10% by weight of alkylaromatic compounds with one or more alkyl groups, which have a total of 8 carbon atoms.

0.5 to 10% by weight of alkylaromatic compounds with one or more alkyl groups, which have a total of 9 carbon atoms.

0.5 to 10% by weight of alkylaromatic compounds with one or more alkyl groups, which have a total of 10 carbon atoms.

The hydrotrope (hydrotropic agent) as such is formed upon sulphonating and neutralizing the hydrotropic precursor, whether isolated or mixed with the linear mono-alkylaromatic.

In a particular embodiment of the present invention, the step vii) purification process is carried out by means of techniques for elimination and/or separation of poly-aromatic and poli-alkylaromatic impurities familiar to an expert on the matter, such as for example, hydrogenation, fractioning and adsorption. In a preferred embodiment, the step vii) purification process is carried out by means of selective adsorption using a selective clay typeadsorbent, which comprises:

a) a total silicon:aluminium molar ratio between 3:1 and 5:1, preferably between 4.1:1.0 b) between 1%-4% by weight of $Fe_2O_3$, preferably 2.9% by weight c) between 0.5%-2% by weight of $K_2O$, preferably 1.4% by weight d) between 0.2%-2% by weight of MgO, preferably 1.2% by weight e) between 0.1-1.0% by weight of $TiO_2$, preferably 0.45% by weight f) between 1800 and 2500 ppm of Na, preferably 2200 ppm by weight g) a specific area referred to as the BET area, comprised between 150-500 $m^2/g$, preferably 260 $m^2/g$;

h) a cumulative pore volume between 0.1-2.0 ml/g, preferably 0.42 ml/g;

i) a macropore distribution where the macropore diameter is comprised between 20-800 angstroms, preferably between 20-200 angstroms, more preferably between 20-100 angstroms, with an average diameter in terms of pore volume centred at 34 angstroms.

In a particular embodiment of the present invention, the hydrotropic to precursor obtained in step iv) is added to the linear mono-alkylaromatic compound stream when the 2 phenyl isomer content of the linear mono-alkylaromatic compounds is equal to or greater than 60% by weight, being added prior to the step vii) purification.

In a particular embodiment of the present invention, the step ix) neutralization process is carried out by means of an alkaline substance comprising one or more cations selected from the group: Na, K, $NH^{4+}$, Mg, Ca, Ba or by means of substituted ammonium alkalis.

In a more particular embodiment of the present invention, the olefins are α-olefins, and they comprise between 9-30 carbon atoms.

In a particular embodiment of the present invention, the temperature of the reaction is comprised between 20-400° C.

In a particular embodiment of the present invention, the spatial rate is comprised between 1 $h^{-1}$ y15 $h^{-1}$ In a particular embodiment the procedure described in the present invention comprises an additional step viii) of sulphonation and neutralization of the compound obtained in step vii).

In a particular embodiment of the present invention, the hydrotropic precursor obtained at step iv) is sulphonated and neutralized individually and subsequently added to the product obtained in step viii)

Another aspect of the present invention refers to a linear sulphonated and neutralized mono-alkylaromatic compound obtained by the procedure described in the present invention.

Another aspect of the present invention refers to a procedure for obtaining a linear mono-alkylaromatic compound with a 2-phenyl isomer content of at least 18% by weight by means of the catalytic alkylation of an aromatic compound with an alkylating agent as described previously, where steps i), ii), iii) and iv) are optional.

Another aspect of the present invention refers to appropriate cleansing compositions for preparations for: dish washing, hard surface cleaning agents, liquid washing products, washing powder products, cleaning preparations in the form of paste, gels and bars for washing, which comprise:
  a) between 1-99% by weight of a compound obtained as from step viii)
  b) between 99-1% by weight of other detergent ingredients selected from the group formed of: derivatives of fatty alcohols, fatty acids, alkyl sulphates, ethanolamines, amine oxides, alkaline carbonates, ethanol, isopropanol, water, pine oil, sodium chloride, sodium silicate, polymers, alcohol alcoxilates, perborate salts, zeolites, alkaline sulphates, enzymes, hydrotropes, colours, fragances, preservatives, polishes, polyacrylates, essential oils, alkaline hydroxides, ether sulphonates, branched alkylbenzene sulphonates soluble in water, alkylphenol alkoxylates, fatty acid amines, alpha-olefin sulphonates, paraffin sulphonates, betaines, chelating agents, Wanin talo ethoxylates, polyetheramine ethoxylates, ethylene oxide/propylene oxide block copolymers, ethoxylated alcohols, propoxylated alcohols, methylester sulphonates, alkylpolysaccharides, n-methylglucamides, sulphonated diphenyl alkyl oxide and polyethyleneglycol

DETAILED DESCRIPTION OF A MODE OF EMBODIMENT

Figure 1:
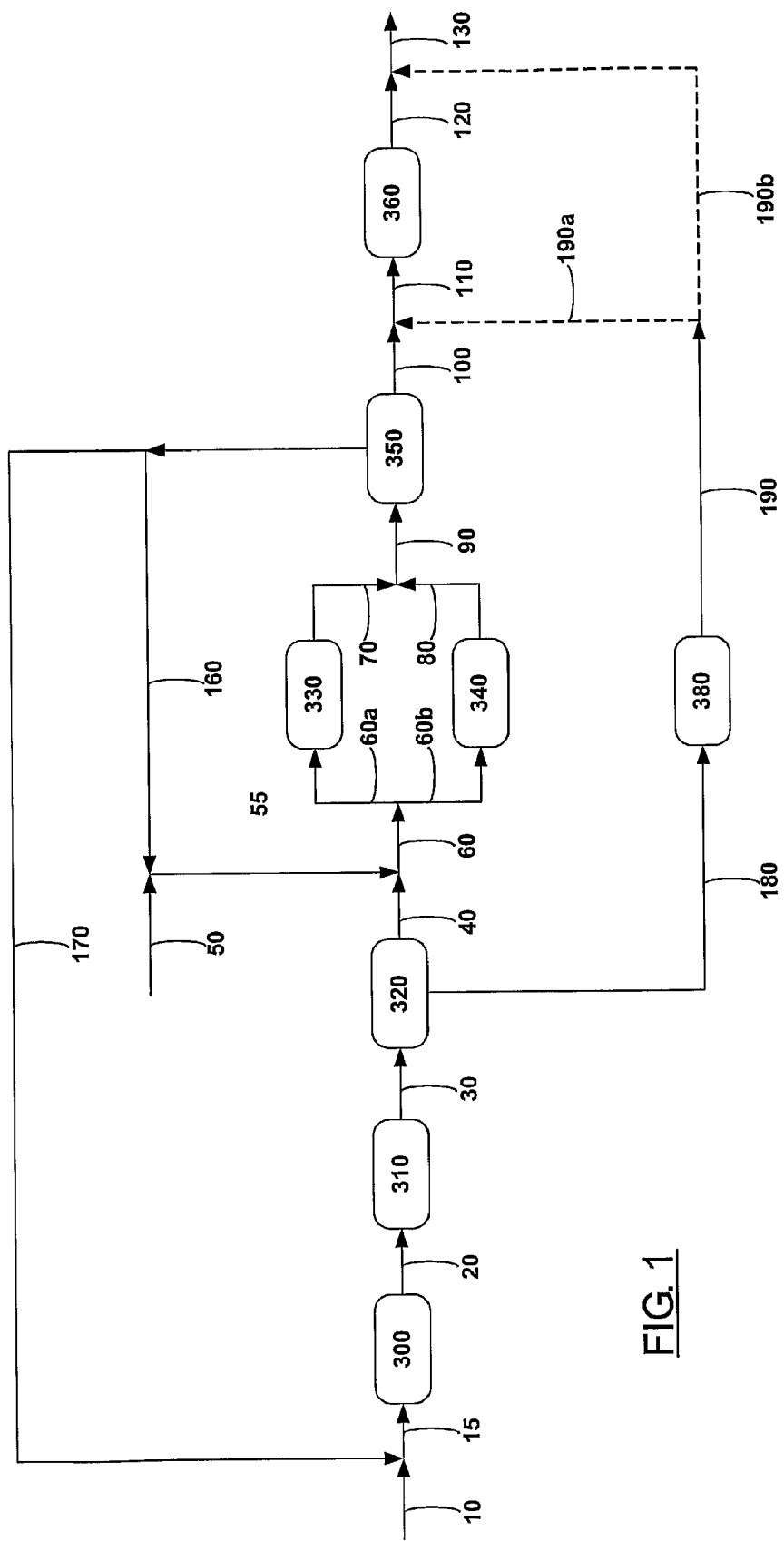
FIG. 1 shows a schema of the process constituting the present invention in the form of a flow diagram.

FIG. 1 represents a non-restrictive diagram for the implementation of this invention.

Flow 15 is the linear paraffin feed to the dehydrogenation unit and comprises the mixture of the fresh linear paraffins, flow 10, with the unconverted linear paraffins separated in the raw alkylate purification unit, unit 350, and recirculated by way of flow 170. Dehydrogenation unit 300 converts the linear paraffin feed into a mixture of linear mono-olefins, non-reacted paraffins and various by-products such as diolefins and non-linear compounds. In this embodiment, in which benzene is used as the aromatic hydrocarbon, raw alkylate is the mixture of mono-alkylbenzenes, non-reacted benzene, paraffins and light and heavy by-products which make up the alkylation step effluent.

The olefin purification unit, unit 310, is fed with the dehydrogenation unit effluent by way of flow 20, increasing the net mono-olefin content by converting some of the by-products generated in the dehydrogenation unit, mainly the diolefins, into mono-olefins, by means of a selective hydrogenation reaction. The resultant flow, flow 30, is processed in unit 320, which contains a selective adsorbent for eliminating the non-linear compounds produced in the dehydrogenation process.

Fresh benzene is pumped to the process by way of flow 50, and it is mixed with recycled benzene that has not reacted (flow 160), which comes from the raw alkylate purification unit, unit 350. The mixture of these two flows forms the benzene feed (flow 55), which is mixed with the effluent (flow 40) from the selective adsorption unit 320 to form flow 60, composed of mono-olefins, benzene and paraffins, which feeds the alkylation units. Flow 60 is divided into two identical flows (in composition but not necessarily in delivery rate), 60a and 60b, which feed two different alkylation reactors, units 330 and 340, respectively; alkylation reactor 330 uses a catalyst which produces an effluent (flow 70) with a raw alkylate whose mono-alkylbenzenes have a maximum 2-phenyl isomer content of 20% by weight, while alkylation reactor 340 uses a catalyst that produces an effluent (flow 80) with a raw alkylate whose mono-alkylbenzenes have a 2-phenyl isomer content of at least 20% by weight. Flows 70 and 80 are mixed to generate a flow, flow 90, composed of a raw alkylate whose mono-alkylbenzenes have a variable 2-phenyl content (according to the delivery rates of flows 60a and 60b), non-reacted benzene, paraffins and light and heavy by-products. Flow 90 feeds the raw alkylate purification unit, unit 350, where the benzene that has not reacted, the paraffins and by-products lighter and heavier than the mono-alkylbenzenes are distilled in order to obtain a relatively pure linear mono-alkylbenzene (flow 100). The paraffins are recirculated to the process by the flow 170, while the benzene is recirculated by flow 160. Flow 100 then feeds the end linear mono-alkylbenzene purification unit, unit 360, which contains a selective adsorbent to eliminate the aromatic compounds that, even in small quantities, are present in the relatively pure mono-alkylbenzene due to the fact that their distillation temperature range overlaps that of the linear mono-alkylbenzene of interest.

The non-linear compounds extracted in unit 320 are pumped to the specific treatment unit 380 via flow 180. This unit 380 comprises fractionating and hydrogenation steps in order to isolate and purify respectively the fraction of on-linear impurities of interest, which constitute the hydrotropic precursor (flow 190). Depending on the specific output needs of the facility at any given time (product with a content of more or less than 60% by weight of 2-phenyl isomers, according to demand at the time), flow 190 may be conveyed via flows 190a or 190b, or it may not be used if the 2-phenyl isomer content of the linear mono-alkylbenzene of flow 100 is less than 60% by weight. Thus, flows 190a and 190b may be dispensed with when the 2-phenyl isomer content in the linear alkylbenzene of flow 100 is below 60% by weight. In this case, the relatively pure linear alkylbenzene of flow 100-110 is purified (unit 360) individually, the effluent of 360 (flow 120) comprising the purified linear. When the 2-phenyl isomer content in the linear mono-alkylbenzene is above 60% by weight, the process may be carried out by two alternative channels. On the one hand, the relatively pure linear mono-alkylbenzene flow, flow 100, and the hydrotropic precursor flow 190a may be mixed to form flow 110, which feeds unit 360 so as to be purified. The effluent of unit 360 (flow 120-130) contains the end linear alkyl-aromatic compound lineal final. On the other hand, flow 190a may be dispensed with, so that the relatively pure linear alkylbenzene lineal which comes from unit 350, flow 100-110, is purified separately in unit 360 and, once purified (flow 120), it is mixed with the hydrotropic precursor supplied by flow 190b, generating flow 130, which comprises the end linear mono-alkylaromatic compound.

Figure 2:
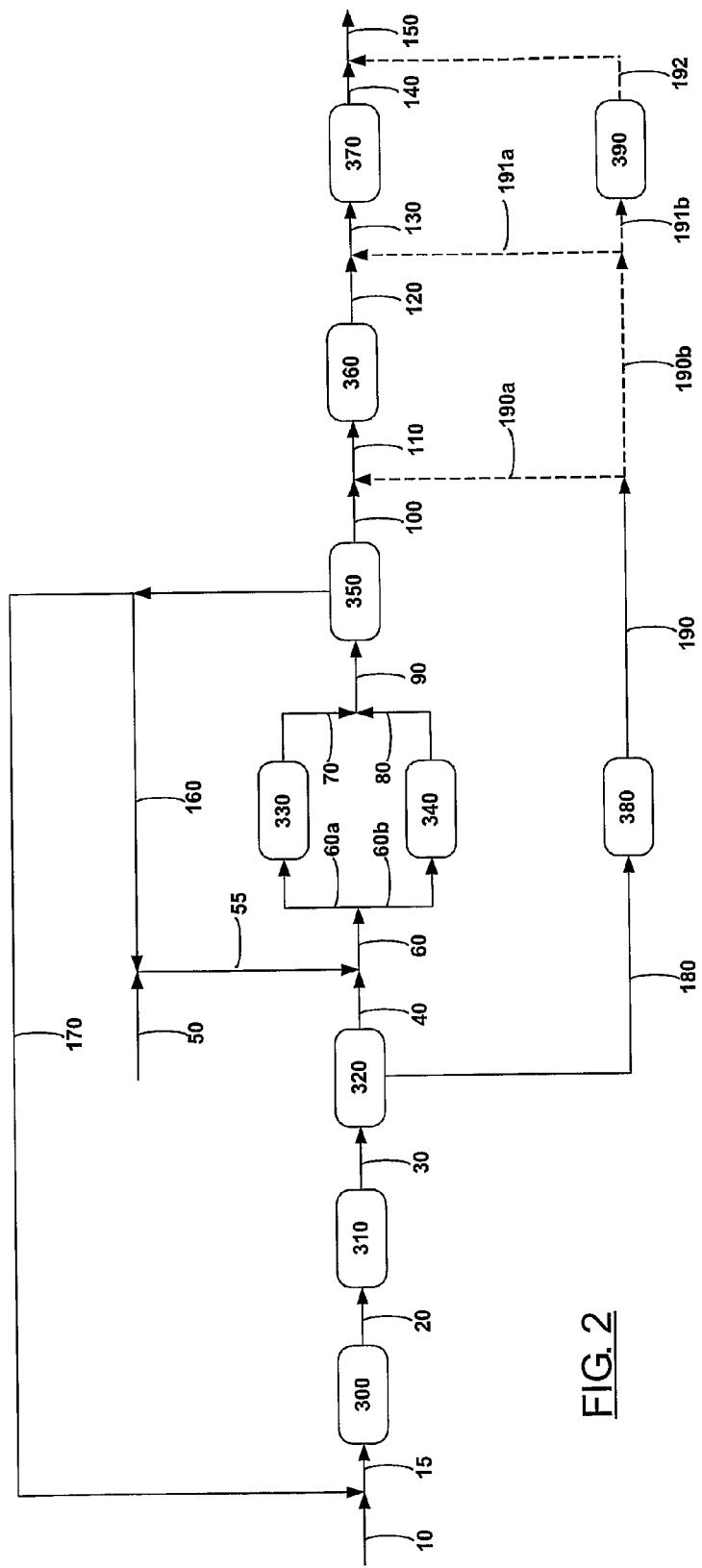
FIG. 2 shows a schema of the process constituting the present invention in the form of a flow diagram in which the sulphonation and neutralization steps are included.

FIG. 2 represents a non-restrictive schema for the implementation of this invention, which includes the sulphonation and neutralization steps.

Flow 15 is the paraffin feeds to the dehydrogenation unit, and it comprises the mixture of the fresh paraffins, flow 10, with the unconverted paraffins separated in the raw alkylate purification unit, unit 350, and recirculated via flow 170. The dehydrogenation unit 300 converts the paraffin feed into a mixture of mono-olefins, non-reacted paraffins and various by-products, such as di-olefins and non-linear compounds. Raw alkylate is taken to be the mixture of mono-alkylbenzenes, non-reacted benzene, paraffins and light and heavy by-product which makes up the alkylation step effluent.

The olefin purification unit, unit 310, is fed with the effluent of the dehydrogenation unit via flow 20, increasing the net mono-olefin content through converting some of the by-products generated in the dehydrogenation unit, mainly the diolefins, into mono-olefins, by means of a selective hydrogenation reaction. The resultant flow, flow 30, is processed in unit 320, which contains a selective adsorbant to eliminate the non-linear compounds produced in the dehydrogenation unit.

Fresh benzene is pumped to the process via flow 50, and it is mixed with recycled benzene that has not reacted (flow 160), which comes from the raw alkylate purification unit, unit 350. The mixture of these two flows forms the benzene feed (flow 55), which is mixed with the effluent (flow 40) from the selective adsorption unit 320 to form flow 60, composed of mono-olefins, benzene and paraffins, which feeds the alkylation units. Flow 60 is divided into two identical flows (rating in composition, not necessary in delivery rate), 60a and 60b, which feed two different alkylation reactors, units 330 and 340 respectively; alkylation reactor 330 uses a catalyst that produces an effluent (flow 70) with a raw alkylate whose mono-alkylbenzenes have a maximum 2-phenyl isomer content of 20% by weight, while alkylation reactor 340 uses a catalyst that produces an effluent (flow 80) with a raw alkylate whose mono-alkylbenzenes have a 2-phenyl isomer content of at least 20% by weight. Flows 70 and 80 are mixed to generate a flow, flow 90, consisting of a raw alkylate whose mono-alkylbenzenes have a variable content in 2-phenyl isomer (according to the delivery rates of flows 60a and 60b), non-reacted benzene, paraffins and light and heavy by-products. Flow 90 feeds the raw alkylate purification unit, unit 350, where the benzene which has not reacted, the paraffins and the by-products lighter and heavier than the mono-alkylbenzenes are fractionated in order to obtain a relatively pure linear mono-alkylbenzene (flow 100). The paraffins are recirculated to the process via flow 170, while the benzene is recirculated via flow 160. Flow 100 then feeds the final linear mono-alkylbenzene purification step, unit 360, which contains a selective absorbent to eliminate the aromatic compounds that are present, even in small quantities, in the relatively pure mono-alkylbenzene due to the fact that distillation temperature range overlaps that of the linear mono-alkylbenzene of interest.

The non-linear compounds extracted in unit 320 are pumped to specific treatment unit 380 via flow 180. This unit 380 comprises fractionating and hydrogenation steps to separate and purify, respectively, the fraction of non-linear impurities of interest, which constitute the hydrotropic precursor (flow 190). Depending on the specific output needs of the facility at any given time (product with a content of more or less than 60% by weight of 2-phenyl isomers, according to demand at the time), flow 190 may be conveyed via flows 190a or 190b, or it may not be used if the 2-phenyl isomer content of the linear mono-alkylbenzene of flow 100 is less than 60% by weight. If the 2-phenyl isomer content in flow 100 is more than 60% by weight, the relatively pure linear mono-alkylbenzene flow, flow 100, and the hydrotropic precursor flow 190a may be mixed to form flow 110, they are purified together in unit 360 and then, via flows 120 and 130, they are sent to unit 370, where they are sulphonated/neutralized together, generating the end flow, flow 140-150. Flow 190a may also be dispensed with, so that the relatively pure linear alkylbenzene lineal which comes from unit 350, flow 100-110, is purified separately in unit 360 and, once purified (flow 120), it is mixed with the hydrotropic precursor supplied by flows 190b and 191a to generate flow 130, being sulphonated and neutralized together in unit 370, thus generating the end flow, flow 140-150. Flows 190a and 191a may also be dispensed with, so that the relatively pure alkylbenzene of flow 100 is purified (unit 360), sulphonated and neutralized (unit 370) separately. The effluent from unit 370 (flow 140) is then mixed with flow 192, corresponding to the hydrotropic precursor sulphonated and neutralized individually. This flow 192 is obtained upon sulphonating and neutralizing the hydrotropic precursor from unit 380 (via flows 190, 190b and 191b) separately in unit 390. End flow 150 is obtained when flows 140 and 192 are mixed. If the 2-phenyl isomer content in flow 100 is less than 60% by weight, flows 190a and 190b are dispensed with, and the linear alkylbenzene is purified isolated in unit 360 and conveyed via flows 120-130 to the sulphonation and neutralization unit (unit 370), whose effluent (flow 140-150) is the end flow of this embodiment.

Figure 3:
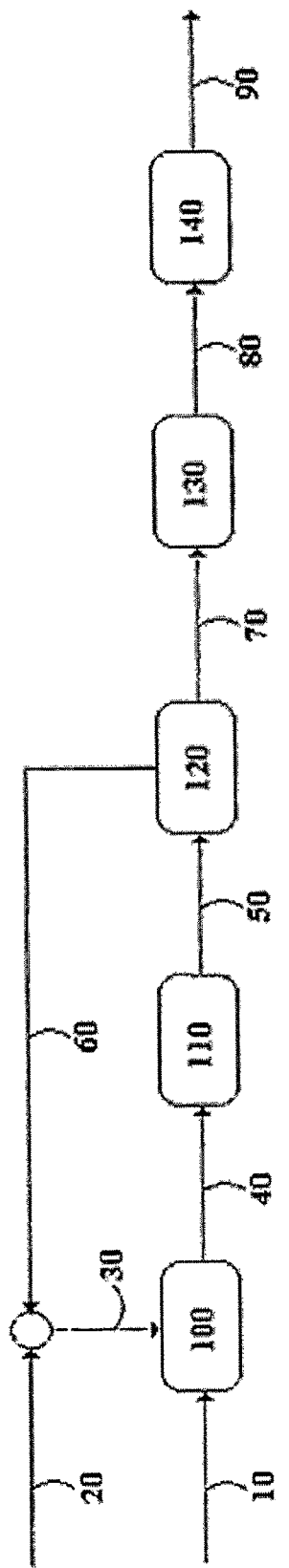
FIG. 3 shows a schema of the reaction of the present invention in the form of a flow diagram when the paraffin catalytic dehydrogenation, diolefin hydrogenation, raw alkylation agent purification and the hydrotropic precursor isolation, purification and addition steps are omitted.

FIG. 3 represents another non-restrictive schema for the implementation of the invention, when steps i), ii), iii) and iv) are optional.

Flow 10 is the feed of fresh olefins to the process. Flow 20 is the fresh feed of the aromatic compound, such as benzene, to the process. Flow 20 is is mixed with flow 60, which constitutes the recycle of the excess aromatic compound once separated from the alkylation products in the distillation column, unit 120. Mixing flows 20 and 60 generates flow 30, which is the aromatic compound feed. This flow 30 is mixed in the mixing unit 100 with flow 10 in order to obtain a mixture of the aromatic compound and the olefins with the desired olefin-to-aromatic molar ratio, flow 40. This flow is fed to the alkylation unit, unit 110, composed of two fixed bed reactors that operate in parallel, where one reactor is charged with the catalyst that produces a raw alkylate whose alkylbenzenes contain less than 20% of 2-phenyl isomers and the other reactor is charged with the catalyst that produces a raw alkylate whose alkylbenzenes contain more than 20% of 2-phenyl isomers. The feed flow (flow 40) is divided into two (with the same composition and not necessarily the same delivery rate) to supply both reactors, where the alkylation of the aromatic compound by the olefins takes place. The effluents from both reactors join together to generate the alkylation unit effluent flow, flow 50, which is made up of the non-reacted aromatic compound and the alkylaromatic compound generated during alkylation. Flow 50 is fractionated in a distillation column, unit 120, in order to separate the aromatic which has not reacted at its upper part, flow 60, and the alkylaromatic compound at its lower part, flow 70. Flow 60 is recirculated to the process, as mentioned above, while flow 70 is sulphonated in a falling film reactor with gaseous $SO_3$, unit 130. The sulphonated product, flow 80, is composed of linear alkylsulphonic acid of high purity, with a given 2-phenyl isomer content. This product may then be neutralized in unit 140 with calcium, barium, sodium, magnesium and ammonium alkaline salts, in the presence of a highly ionizable compound, such as phenol, in order to obtain a highly pure alkylaromatic sulphonate, both neutral and preferably superbasic, depending on the quantity of base used in the neutralization.

The invention is described additionally, for illustrative purposes only, by way of the following examples, which should never be considered as factors limiting the scope of the present invention.

EXAMPLES

Example 1

This example refers to the method to obtain the purified alkylating agent and the method to obtain the hydrotropic precursor from the impurities extracted during the purification of said alkylating agent.

The process starts with a mixture of high-purity linear paraffins (content in regular paraffins should be above 97 wt %, according to the UOP 411 method), carbon atom distribution in the paraffins should be as stated in table 1:

TABLE 1

| Initial Linear Paraffin Distribution | Wt % of each paraffin |
|---|---|
| <$C_{10}$ | 0.5 |
| $C_{10}$ | 11 |
| C11 | 34 |
| C12 | 32 |
| C13 | 22 |
| C14 | 1 |

These linear paraffins underwent a process of selective dehydrogenation towards mono-olefins; using a typical commercial catalyst for the selective dehydrogenation of detergent-range paraffins. Dehydrogenation conditions are summarized in table 2, and provide a yielding of olefins of 14%:

TABLE 2

| Pressure (bar) | 1.3-1.5 |
|---|---|
| Temperature (° C.) | 469-472° C. |
| H2/Hydrocarbon Molar ratio | 3.0-5.0 |
| LHSV ($h^{-1}$)(*) | 20-23 |

(*)Note: LHSV: Liquid Hourly Space Velocity

The effluent from the dehydrogenation step may contain up to 0.1 wt % of diolefins, which are the undesired by-products from the dehydrogenation step. For this reason, the effluent from the dehydrogenation step undergoes a purification process. During such purification process, the effluent from the dehydrogenation step undergoes a process of selective hydrogenation in order to turn the undesired diolefins into desired mono-olefins. To that end, a Ni—Mo type commercial catalyst is used. Selective dehydrogenation conditions are summarized in table 3:

TABLE 3

| Pressure (bar) | 9-11 |
|---|---|
| Temperature (° C.) | 190-200° C. |

LHSV conditions are adjusted (liquid load/catalytic bed volume ratio) in order to obtain a conversion of diolefins to mono-olefins above 99%, this conversion is tested with the UOP 902-89 method. The resulting mixture of mono-olefins and paraffins constitutes the non-purified alkylating agent.

The purification step of the alkylating agent is carried out by means of an adsorbent bed, where a certain amount of a particular molecular sieve is placed. The selected molecular sieve is a 13X type zeolite, widely used in processes of selective elimination of non-linear components from a mixture of olefins and paraffins. The mixture of olefins and paraffins goes through the bed in order to achieve a selective adsorption of the non-linear components proceeding from the previous dehydrogenation step (or which are present in the fresh paraffin feed and/or paraffin recycling). Once the bed is saturated with non-linear components, the bed is washed with short-chain paraffins to desorb the olefins and paraffins which may have been retained in the pores, and it is then washed with benzene to desorb the previously adsorbed non-linear components which may later be turned into the hydrotropic precursor. Operation conditions for a pilot plant for the purification step are summarized in table 4:

TABLE 4

| Particular size (Standard US Mesh) | 10 to 20 |
|---|---|
| Adsorption temperature (° C.) | 135-145 |
| Washing temperature (° C.) | 123-135 |
| Desorption temperature (° C.) | 135-145 |
| Adsorption pressure (kg/$cm^2$) | 25 |
| Washing pressure (kg/$cm^2$) | 25 |
| Desorption pressure (kg/$cm^2$) | 25 |
| Washing agent | n-pentane |
| Desorption agent | benzene |
| LHSV ($h^{-1}$) | 1.5-2.5 |

The mixture of olefins and paraffins from the selective dehydrogenation and hydrogenation, that is, the non-purified alkylating agent, contains approximately 2 wt % of non-linear components. The constitution of the alkylating agent purified through the adsorption of non-linear components in the zeolite 13X is summarized in table 5:

TABLE 5

| Compound | Percentage (wt % in the mixture) |
|---|---|
| n-C10 | 14.8 |
| n-C11 | 31.0 |
| n-C12 | 26.1 |
| n-C13 | 18.2 |
| n-C14 | <0.9 |
| C10-olefin | 1.3 |
| C11-olefin | 3.2 |
| C12-olefin | 3.1 |
| C13-olefin | 2.3 |
| C14-olefin | <0.1 |
| Aromatic Compounds | <0.1 |

The non-linear components separated during the purification step of the alkylating agent constitute the raw material needed to obtain the hydrotropic precursor. There follows a description of the method for the transformation of said impurities into the hydrotropic precursor. When washed with benzene after the purification of the alkylating agent, the non-linear impurities desorbed from the X13 zeolite undergo an atmospheric fractionation step. During the fractionation step, the aim is to separate the benzene used in desorption (the benzene shall later be recirculated into the 13X zeolite desorption cycle) and the impurities which have no hydrotropic potential (poly-aromatic species with high molecular weight) from the fraction of species which have hydrotropic potential. It has been found that the fraction of species with hydrotropic potential (those which provide a hydrotropic effect when sulfated and neutralized) for the LAS, object of this invention, is the fraction that distills at a temperature range of 195° C.-259° C. Once this fraction has been isolated by means of atmospheric distillation, it undergoes a hydrogenation process in order to eliminate the components which may form colored species when sulfated. Hydrogenation conditions are stated in table 6:

TABLE 6

| Pressure (bar) | 20-30 |
|---|---|
| Temperature (° C.) | 185-195 |
| mol H2/mol hidrocarbon | 1-2 |
| LHSV ($h^{-1}$) | 4-8 |

The resulting product from this hydrogenation step constitutes the hydrotropic precursor whose composition is described in table 7:

TABLE 7

| Distribution | Wt % |
|---|---|
| Phenyl-$C_4$ | 7 |
| Phenyl-$C_5$ | 20 |
| Phenyl-$C_6$ | 25 |
| Phenyl-$C_7$ | 15 |
| Phenyl-$C_8$ | 7 |
| Phenyl-$C_9$ | 7 |
| Phenyl-$C_{10}$ | 7 |
| Total content of alkyl-aromatic species | 88 |
| Other compounds | 12 |
| Average molecular weight (g/mol) | 165 |
| Bromine rate (ASTM D 1491 method) | 130 |

Example 2

This example refers to the advantages of using a catalyst based on a zeolite Y, with a high content of rare earths (such as La, Ce, Nd and Pd) and sodium, in comparison to a catalyst based on a zeolite Y, with a low content of rare earths (such as La, Ce, Nd and Pd) and sodium, in the process of benzene alkylation with a purified mixture of detergent range olefins/paraffins. Specifically, two catalysts are compared. On one hand, a catalyst (catalyst A) based on a zeolite Y with a total content of 7% rare earth metals and low sodium (0.1 wt %); and on the other hand, a catalyst (catalyst B) based on a zeolite Y with a content of rare earth metals 71% higher (12 wt % of rare earth metals) and a content sodium 90% higher (0.9 wt %).

Both catalysts were tested by using same size extruded particles. The benzene was dried by means of a molecular sieve in order to minimize water addition, and after that, the benzene was mixed with a mixture of purified mono-olefins and paraffins (purified alkylating agent, see example 1). The alkylation tests in pilot plant were conducted in a fixed bed isothermal reactor, with 24-hour-reaction cycles followed by catalyst-regeneration cycles by benzene washing during the same period of time. A standard cycle consists of a 24-hour-reaction cycle at 140° C., LHSV=11 h$^{-1}$, and a benzene:olefin molar ratio of 30:1, followed by a benzene washing cycle during the same period of time. The catalyst weight, the washing conditions etc., are summarized in table 8:

TABLE 8

| Operation Conditions | |
|---|---|
| Extruded Particle Size (mm × mm) | 1.5 × 5.0 |
| Catalyst Volume (cm$^3$) | 122 |
| Reaction Temperature (° C.) | 100-150 |
| Regeneration Temperature (° C.) | 260 |
| Reaction Pressure (kgf/cm$^2$) | 20 |
| Regeneration Pressure (kgf/cm$^2$) | 40 |
| Reaction LHSV (h$^{-1}$) | 4-11 |
| Regeneration LHSV (h$^{-1}$) | 1 |
| Benzene/Olefin Molar Ratio | 10-30 |

The composition of the initial raw material, which refers to the mixture of olefins and paraffins, is summarized in table 9:

TABLE 9

| Compound | Percentage (wt % in the mixture) |
|---|---|
| n-C10 | 14.8 |
| n-C11 | 31.0 |
| n-C12 | 26.1 |
| n-C13 | 18.2 |
| n-C14 | <0.9 |
| C10 olefin | 1.3 |
| C11 olefin | 3.2 |
| C12 olefin | 3.1 |
| C13 olefin | 2.3 |
| C14 olefin | <0.1 |
| Aromatic Compounds | <0.1 |

This purified mixture of paraffins and olefins (purified alkylating agent, see example 1) is mixed with the dried benzene until the desired benzene:oleofin molar ratio is reached. The catalyst tests were conducted in four different sequences of reaction cycles. Once each reaction cycle has been developed, the alkylation effluent (raw alkylate, comprising the alkylbenzene formed, the non-reacted benzene, the paraffins and heavy alkylate) was distilled in three steps by using three consecutive distillation columns (the first of these columns operating under atmospheric pressure, while the others operating under vacuum). The first column operated at atmospheric pressure, and separated the non-reacted benzene in its upper part, while the compounds in its bottom were fed to the second column. The second column separated paraffins in its upper part, while the compounds in its bottom fed the third column. The third column is separated the mono-alkylbenzenes in its upper part, and the heavy alkylate in its lower part. The tests (conducted by GC-FID) refer to the compounds fed to the third column. Throughout all the examples described in this patent, the chromatographic method, reference U 698, has been used. During the first sequence of reaction cycles, both catalysts (A and B) were independently tested under the same operation conditions. For each catalyst, the evaluation sequence consisted of seven reaction cycles carried out by means of a 11 h$^{-1}$ LHSV at temperatures between 130 and 140° C., followed by three cycles at 115° C., with a 4 h$^{-1}$ LHSV. Next, a standard cycle was completed at 140° C., and an 11 h$^{-1}$ LHSV in order to verify the catalyst deactivation. In all these cycles, the benzene-olefin molar ratio was kept at 30:1. Each of these reaction cycles was followed by a regeneration cycle (washing cycle). All conditions and results are summarized in table 10. Note that the difference to 100% of the addition of mono-alkylbenzenes and heavy alkylate corresponds to light by-products (lower than 5-phenyl-$C_{10}$), while the difference to 100% of the addition of branched alkylate and 2-phenyl isomers corresponds to inner isomers (3, 4, 5 and 6-phenyl).

TABLE 10

| | | | Conversion (% mol) | | Mono-alkylbenzene (wt %) | | Heavy Alkylate (wt %) | | Branched Alkylate (wt %) | | 2-phenyl Isomers (wt %) | |
|---|---|---|---|---|---|---|---|---|---|---|---|---|
| Cycle | T (° C.) | LHSV (h⁻¹) | A | B | A | B | A | B | A | B | A | B |
| 1 | 140 | 11 | 100.0 | 100.0 | 98.4 | 98.6 | 0.6 | 0.5 | 6.5 | 3.7 | 18.7 | 19.3 |
| 2 | 140 | 11 | 100.0 | 100.0 | 98.5 | 98.6 | 0.5 | 0.4 | 6.4 | 3.6 | 18.5 | 19.2 |
| 3 | 140 | 11 | 100.0 | 100.0 | 98.8 | 98.8 | 0.3 | 0.3 | 6.3 | 3.6 | 18.5 | 19.2 |
| 4 | 130 | 11 | 99.9 | 99.9 | 98.4 | 98.5 | 0.7 | 0.5 | 5.7 | 3.7 | 18.4 | 19.1 |
| 5 | 130 | 11 | 99.9 | 99.9 | 98.4 | 98.5 | 0.7 | 0.5 | 6.0 | 3.9 | 18.3 | 19.1 |
| 6 | 130 | 11 | 99.9 | 99.9 | 98.5 | 98.7 | 0.6 | 0.4 | 5.8 | 3.8 | 18.4 | 19.1 |
| 7 | 140 | 11 | 100.0 | 100.0 | 98.5 | 98.6 | 0.5 | 0.4 | 6.9 | 3.9 | 18.4 | 19.2 |
| 8 | 115 | 4.0 | 100.0 | 100.0 | 98.3 | 98.4 | 0.8 | 0.7 | 5.1 | 3.3 | 18.5 | 19.0 |
| 9 | 115 | 4.0 | 100.0 | 100.0 | 98.3 | 98.4 | 0.8 | 0.7 | 5.2 | 3.4 | 18.4 | 19.0 |
| 10 | 115 | 4.0 | 100.0 | 100.0 | 98.4 | 98.6 | 0.8 | 0.7 | 5.2 | 3.4 | 18.4 | 19.1 |
| 11 | 140 | 11 | 100.0 | 100.0 | 98.4 | 98.5 | 0.6 | 0.5 | 6.8 | 3.9 | 18.4 | 19.2 |

During the second sequence of reaction cycles, kinetic tests were conducted on catalysts A and B in order to analyze their activity in lower temperatures. This sequence comprised three reaction cycles carried out to a 4 h⁻¹ LHSV, but this time at 100° C., followed by a standard cycle (LHSV=11 h⁻¹; T=140° C.). In all these cycles, the benzene-olefin molar ratio was kept at 30. All conditions and results are summarized in table 11. Note that the difference to 100% of the addition of mono-alkylbenzenes and heavy alkylate corresponds to light by-products (lower than 5-phenyl-$C_{10}$)), while the difference to 100% of the addition of branched alkylate and 2-phenyl isomers corresponds to inner isomers (3, 4, 5 and 6-phenyl).

TABLE 11

| | | | Conversion (% mol) | | Mono-alkylbenzene (wt %) | | Heavy Alkylate (wt %) | | Branched Alkylate (wt %) | | 2-phenyl Isomers (wt %) | |
|---|---|---|---|---|---|---|---|---|---|---|---|---|
| Cycle | T (° C.) | LHSV (h⁻¹) | A | B | A | A | A | B | A | B | A | B |
| 1 | 100 | 4.0 | 99.9 | 99.9 | 98.3 | 98.4 | 1.1 | 0.9 | 3.8 | 2.5 | 18.2 | 18.8 |
| 2 | 100 | 4.0 | 99.9 | 99.9 | 98.5 | 98.5 | 0.9 | 0.8 | 3.8 | 2.5 | 18.2 | 18.8 |
| 3 | 100 | 4.0 | 99.9 | 99.9 | 98.6 | 98.7 | 0.8 | 0.7 | 4.0 | 2.6 | 18.2 | 18.7 |
| 4 | 140 | 11.0 | 100.0 | 100.0 | 98.5 | 98.6 | 0.6 | 0.5 | 6.7 | 3.8 | 18.4 | 19.2 |

The third sequence of reaction cycles comprised six reaction cycles, carried out with LHSV, variable temperatures and benzene-olefin molar ratio in order to analyze the effect of the last variable on the conversion and selectivity of the reaction. Conditions and results are summarized in table 12:

TABLE 12

| | | | | Conversion (% mol) | | Mono-alkylbenzene (wt %) | | Heavy Alkylate (wt %) | | Branched Alkylate (wt %) | | 2-phenyl Isomers (wt %) | |
|---|---|---|---|---|---|---|---|---|---|---|---|---|---|
| Cycle | T (° C.) | LHSV (h⁻¹) | Bz/Olef | A | B | A | B | A | B | A | B | A | B |
| 1 | 120 | 3.1 | 10 | 100.0 | 100.0 | 94.9 | 95.0 | 3.3 | 3.2 | 7.6 | 4.9 | 18.8 | 19.2 |
| 2 | 120 | 3.6 | 15 | 100.0 | 100.0 | 96.6 | 96.8 | 1.9 | 1.7 | 6.7 | 4.4 | 18.8 | 19.2 |
| 3 | 120 | 4.5 | 25 | 100.0 | 100.0 | 97.2 | 97.5 | 1.3 | 1.0 | 6.5 | 4.2 | 18.7 | 19.2 |
| 4 | 120 | 4.9 | 30 | 100.0 | 100.0 | 98.0 | 98.1 | 0.7 | 0.6 | 5.9 | 3.8 | 19.1 | 19.6 |
| 1 | 140 | 3.1 | 10 | 100.0 | 100.0 | 94.4 | 94.6 | 4.0 | 3.8 | 9.1 | 5.2 | 19.0 | 19.5 |
| 2 | 150 | 3.1 | 10 | 100.0 | 100.0 | 94.9 | 95.0 | 4.0 | 3.8 | 10.2 | 5.8 | 18.9 | 19.3 |

During the fourth sequence of reaction cycles, both catalysts were tested in order to analyze their deactivation speed. Aiming at forcing the deactivation of the catalyst, after an initial standard cycle (LHSV=11 h$^{-1}$; T=140° C.), the usual 24-hour reaction period was extended to 72 hours with no standard benzene washing every 24 hours. During all these cycles, the benzene-olefin molar ratio was kept at 30. The catalyst activity was analyzed in conversion terms. All results and conditions are summarized in table 13:

TABLE 13

| Reaction hours | Temperature (° C.) | LHSV (h$^{-1}$) | Catalyst A Conversion | Catalyst B Conversion |
|---|---|---|---|---|
| 24 | 140 | 11 | 100.0 | 100.0 |
| 30 | 140 | 11 | 100.0 | 100.0 |
| 36 | 140 | 11 | 100.0 | 100.0 |
| 42 | 140 | 11 | 99.9 | 99.9 |
| 48 | 140 | 11 | 99.9 | 99.9 |
| 54 | 140 | 11 | 99.5 | 99.7 |
| 60 | 140 | 11 | 98.9 | 99.6 |
| 66 | 140 | 11 | 98.2 | 99.5 |
| 72 | 140 | 11 | 97.1 | 99.5 |

As can be observed in table 10, the activity of catalyst B is equal to that of catalyst A in all the sequences of 24-hour-reaction cycles since, as in catalyst A, catalyst B provides conversion levels between 99.9 and 100% throughout the cycles at "high" temperature (from 115° C. to 140° C.). In terms of conversion, it can be observed that also during the cycles at "low" temperature (100° C., table 11), said catalyst B can provide a 99.9% activity, which is equal to catalyst A. Furthermore, table 12 shows that both catalysts also yield conversion rates of 100% when LHSV, temperature and benzene-olefin molar ratio vary within industrial operation levels. In terms of catalytic activity, the great advantage of catalyst B is that it provides a short-term activity rate (24-hour cycles) equal to that of catalyst A, but catalyst B is also capable of keeping comprehensive conversion rates (above 99.5%) during longer periods of time (30% more time) with no washing cycles in between, as seen in the forced deactivation tests described in table 13. This greater stability of catalyst B when deactivated due to dirt allows extending the duration of reaction cycles and reducing the number of regeneration cycles needed to operate under comprehensive conversion rates with respect to catalyst A. This provides, for the same period of operation time of catalysts A and B, a longer net operation time while the reaction time of catalyst B is taking place (higher productivity of catalyst B), as well as a reduction in the regeneration net costs (lower number of washing cycles throughout said period of time), mainly regarding power consumption.

In comparison to catalyst A, apart from equivalent activity and more stability when deactivated, catalyst B provides higher selectivity towards the linear mono-alkylated products of interest. In this way, catalyst B yields an average of 30 to 35% less branched alkylate, and between 10 and 18% less heavy alkylate (mainly di-alkylbenzenes) than catalyst A. The reduction of both undesired by-products entails two operational advantages in comparison to catalyst A.

The main advantage of catalyst B refers to the reduction in the production of branched alkylate; therefore, there is a proportional reduction of "inner quaternary carbons." The second advantage associated to catalyst B in relation to catalyst A is that catalyst B produces less heavy alkylate. By reducing the final content of heavy alkylate, there is an enhancement in the use of raw materials during the process towards the formation of mono-alkylated species (di-alkyl-benzenes use an extra olefin chain in comparison to a mono-alkylbenzene molecule). Furthermore, the quality of the final product is considerably enhanced since said heavy alkylate does not behave as efficiently as the mono-alkylated species do during the washing process, and, heavy alkylate frequently interferes in the formation of chromophore by-products during the final sulphonation step, this is why, as seen in example 6, a LAB can be produced with a lower sulphonation color (in relation to 3 units in the Klett-Summerson scale).

Example 3

This example refers to the advantages of using a purified alkylating agent (purified mixture of olefins and paraffins, according to example 1) during the alkylation step. Furthermore, this example refers to the advantages of using a catalyst based on a zeolite Y with higher loads of rare earth metals (12 wt % of rare earth metals in the final catalyst, catalyst B from example 2) in comparison to a catalyst based on a zeolite Y with lower loads of rare earth metals (7 wt % of rare earth metals in the final catalyst, catalyst A from example 2), when using a purified alkylating agent.

The alkylation reaction was carried out with the catalysts A and B described in example 2. In this case, purified and non-purified alkylating agents were used to for each catalyst in order to record behavior differences in the catalysts. Once the alkylating agent has been purified (and above 95% of aromatic elements have been eliminated), the mixture of olefins and paraffins was mixed with dried benzene in order to obtain the selected molar ratio. Later, this mixture was used as feed during the alkylation step. Operation conditions for the alkylation step are summarized in table 14.

TABLE 14

| Temperature (° C.) | 140 |
|---|---|
| Pressure (kgf/cm$^2$) | 20 |
| LHSV (h$^{-1}$) | 11 |
| Benzene/olefin Molar Ratio | 30 |

Another test was conducted in order to analyze the effects that the purification step would have on product distribution, keeping all the operation variables, but this time a non-purified mixture of alkylating agent was used. On the other hand, the raw alkylate distillation process which constitutes the effluent of the alkylation reactor is carried out in order to separate the benzene, paraffins, mono-alkylbenzenes and heavy alkylate, and this process is equivalent to the one defined in example 2. The GC analyses refer to the stream which is fed to the third column (U 698 method). Light elements are analyzed by GC-FID on the effluent of the first column.

Distribution of the product in relation to alkylation with purified and non-purified mixtures in catalysts A and B is summarized in table 15.

TABLE 15

| | Purified Mixture | | Non-purified Mixture | |
|---|---|---|---|---|
| Product Distribution | A | B | A | B |
| Mono-alkylbenzene (wt %) | 98.6 | 98.7 | 94.7 | 95.2 |
| Heavy Alkylate (wt %) | 0.5 | 0.4 | 3.7 | 3.5 |
| Light by-products (wt %) | 0.9 | 0.9 | 1.6 | 1.3 |

As can be observed in table 15, in comparison to non-purified mixtures, the amount of heavy alkylate generated when purified mixtures are used is reduced in 86% in catalyst A, and reduced in 89% in catalyst B. Also, it is observed that the purification of the paraffin/olefin mixture contributes to a reduction of light by-products, this reduction is slightly higher in catalyst A (44% reduction) than in catalyst B (30% reduction). In any case, it is shown that the purification of the paraffin/olefin mixture entails a remarkable reduction in the formation of undesired by-products (above 85% with both catalysts). Besides, in purified as well as non-purified mixtures, catalyst B produces less light and heavy by-products than catalyst A does.

Example 4

This example refers to the higher stability achieved during deactivation of the catalyst based on zeolite Y additivated with higher loads on rare earth metals (12 wt % of rare earth metals in the final catalyst, catalyst B from example 2) in comparison to the catalyst based on a zeolite Y additivated with lower loads of rare earth metals (7 wt % of rare earth metals in the final catalyst, catalyst A from example 2), when the former is used as catalyst in benzene alkylation with a purified alkylating agent. A long sequence of reaction cycles has been carried out for both catalysts A and B, in order to analyze their deactivation rate. Unlike the case of "reversible" deactivation (meaning it can be eliminated by washing) tested in example 2 (table 13), in this case the aim is to study "irreversible" deactivation, that is, the deactivation which does not disappear after catalyst regeneration. All thirty cycles were carried out at LHSV=11 $h^{-1}$, T=140° C. and a benzene:olefin molar ratio of 30 (mixture of purified olefin-paraffin as stated in example 1, composition of the mixture described in tables 5 and 9, remaining operation conditions as stated in table 8). After each 24-hour reaction cycle, a benzene washing cycle was carried out during 24 hours. Results are summarized in table 16, and represent an average of the cycles taken into account.

TABLE 16

| | Average Conversion | |
|---|---|---|
| Cycles | A | B |
| 1 to 10 | 99.6 | 99.8 |
| 11 to 20 | 99.6 | 99.8 |
| 21 to 30 | 99.6 | 99.8 |

As can be observed in table 16, throughout this sequence of reaction/regeneration cycles, the average conversion of catalyst B remained steady and constant (99.8%), along with a value above the one provided by catalyst A. None of the catalysts showed any loss of irreversible activity during the thirtieth cycle in comparison to the initial cycles. By operating catalyst B under higher activity rates than catalyst A, and, as no irreversible deactivation is detected, it can be verified that catalyst B resistance to irreversible deactivation is, at least, equal to that of catalyst A. This allows catalyst B to have a life spam equal to or even longer than that of catalyst A.

Example 5

This example refers to the advantages of using a catalyst based on a zeolite Y containing high loads of rare earth metals and sodium (catalyst B from example 2) in comparison to the use of a catalyst based on a zeolite Y containing low loads of rare earth metals and sodium (catalyst A from example 2) when operating with two parallel, isothermal, fixed bed reactors used to produce alkylate with adjustable contents of 2-phenyl isomers. One of the reactors is loaded with one of the catalysts A or B, and the other reactor is loaded with a non-fluorinated, commercial, crystalline mordenite called catalyst C, adjusting the distribution of the previously purified feed (according to example 1) between the two reactors and mixing the resulting effluents in order to obtain a 2-phenyl isomer adjustable content in the resulting effluent.

A certain amount of catalyst A was placed on one of the fixed bed reactors (called bed 1), while the other bed (called bed 2) was loaded with a certain amount of non-fluorinated, commercial, crystalline mordenite (catalyst C). The feed composition for both reactors was the same. The feedstream was formed by mixing a purified mixture of olefins and paraffins (composition of the mixture as described in table 5, example 1) with an appropriate amount of dried benzene in order to obtain the desired benzene-olefin molar ratio. Said starting stream was always kept at a constant flow. After this, the stream was divided into two sub-streams by means of a three-way valve. Each stream fed a reactor (after a preheating step), in order to dose a variable flow to each reactor by controlling the valve (but keeping the constant the total flow). The effluent emerging from each reactor (raw alkylate) was mixed, thus generating the final effluent which was analyzed by GC-FID (after separating the benzene, the paraffins and the heavy alkylate from the mono-alkylbenzene by means of a distillation process, as stated in example 2). In this example, both the feed composition as well as the reaction pressure were kept at a constant level for both reactors, but the reaction temperature was different in each reactor (since zeolites Y are more active than mordenite), and the feed flow was varied in order to modify the final 2-phenyl isomer content. The same process was carried out by loading bed 1 with catalyst B (same B mass as the one used in A in the previous test), and loading bed 2 with the same amount of catalyst C as the amount used in the previous test, in order to see the difference as regards behavior of both catalysts based on zeolites Y (A and B). Operation conditions are summarized in table 17.

Note that the Liquid Hourly Space Velocity (LHSV) associated with each reactor varies when varying the initial feed percentage dosed to each reactor, from 2.7 $h^{-1}$ (when 25% of the initial feed goes through said reactor) to 11 $h^{-1}$ (when 100% of the initial feed goes through one single reactor).

TABLE 17

| | Catalytic Bed | |
|---|---|---|
| | 1 | 2 |
| Loaded Catalyst | A or B | C |
| Particle Diameter (cylindrically extruded. mm*mm) | 1.5 * 5.0 | 1.5 * 5.0 |
| Catalyst Volume (cm$^3$) | 122 | 122 |
| Reaction Temperature (° C.) | 100 | 140 |
| Reaction Pressure (kgf/cm$^2$) | 20 | 20 |
| LHSV ($h^{-1}$) Reaction | 2.7-11.0 | 2.7-11.0 |
| Benzene/olefin Molar Ratio | 30 | 30 |

Product distribution in the final effluent when the feedstreams are modified, are summarized in table 18.

TABLE 18

| % of Initial Dosed Feed to Each Reactor (bed 1/ bed 2) | Total Conversion (%) | | 2-Phenyl Isomer Content (wt %) | | Heavy Alkylate (wt %) | | Branched Alkylate (wt %) | |
|---|---|---|---|---|---|---|---|---|
| | A | B | A | B | A | B | A | B |
| 100/0 | 99.9 | 99.9 | 18.2 | 18.8 | 0.9 | 0.7 | 6.3 | 2.5 |
| 75/25 | 99.4 | 99.5 | 30.1 | 31.6 | 0.9 | 0.7 | 5.7 | 2.8 |
| 50/50 | 99.1 | 99.2 | 43.0 | 44.4 | 0.9 | 0.8 | 5.1 | 3.1 |
| 25/75 | 98.7 | 98.7 | 55.2 | 57.2 | 0.9 | 0.8 | 4.4 | 3.5 |
| 0/100 | 98.3 | 98.3 | 70.0 | 70 | 0.9 | 0.9 | 3.8 | 3.8 |

As can be observed in table 18, variation of the flow feeding each reactor implies a variation in the final 2-phenyl isomer content in the mono-alkylbenzene, from 18 wt % (obtained when the total initial feed goes through bed 1), to 70 wt %

(obtained when the total initial feed goes through the mordenite bed). It is verified that the process configuration using catalyst B in bed 1 yields a net conversion slightly higher than the net conversion yielded when catalyst A is used, this is due to greater activity of catalyst B at low temperatures. Regarding the formation of 2-phenyl isomers, there are no essential differences between the results obtained when using catalysts A or B. As to the formation of heavy alkylate, it is observed that for bed 1/bed 2 feed dosing ratios lower than or equal to 50/50, when using catalyst B in bed 1, the heavy alkylate final content produced is lower (11 to 20%) than the heavy alkylate produced when using catalyst A in bed 1, which implies a better use of raw materials.

The most significant result from table 18 refers to the production of branched products. Table 18 shows that, when using catalyst B in bed 1, the final amount of branched alkylate in the stream resulting from the mixture of effluents from beds 1 and 2, is much lower than the final amount of branched alkylate produced when using catalyst A. The same range of 2-phenyl isomers can be obtained by using catalyst A or B, but when using catalyst B, conversion and selectivity conditions are enhanced and the amount of branched alkylates in the final product (average content 3.1%) is significantly reduced (up to 60%), the amount of branched alkylates in the final product does not exceed 3.8% in any case. The percentage of branched alkylate produced by means of the B-C catalytic system ranges within the same level than the percentage of branched alkylate produced by means of the existing HF and DETAL technologies which, as mentioned in the state of the art, produce LAB, quickly and completely biodegradable.

Example 6

This example refers to the advantages of purifying the mono-alkylbenzene coming from the raw alkylate alkylation and purification step (described in example 5), before sulphonation step, in order to minimize the sulphonation color of the final sulphonic acid. This example also refers to the advantage of using the catalyst based on a zeolite Y with high loads of rare Earth metals and sodium (catalyst B from example 2), in comparison to the catalyst based on a zeolite Y with low loads of rare earth metals and sodium (catalyst A from example 2), this comparison is based in terms of lower levels of final sulphonation color.

As described in examples 2-5, a purified mixture of olefins and paraffins mixed with dried benzene was used as feed. A 20:1 benzene:olefin molar ratio was selected. Alkylation was carried out by means of two isothermal, parallel fixed bed reactors, as described in example 5. Catalyst A or B was loaded on one of the beds (bed 1), and catalyst C described in example 4 was loaded on the other bed. Operation conditions during the alkylation step were exactly the same as the operation conditions seen in example 5 (table 17). A feed dosing of 50% of the initial stream for each reactor was selected in the configuration in which load bed 1 was loaded with catalyst A as well as the configuration in which bed 1 with catalyst B. The raw alkylate formed by the mixture of effluents from beds 1 and 2 was purified by fractioning in order to isolate the mono-alkylbenzenes. Distillation (purification) of raw alkylate was slightly different when compared to the purification used in previous examples. Four distillation columns were used in this example. The first column operated at atmospheric pressure, and separated the non-reacted benzene in its upper part, while the compounds in its bottom were fed to the second column. The second column, which was vacuum operated, separated the paraffins in its upper part, while the compounds in its bottom were fed to the third column. The third column, which was vacuum operated, separated the mono-alkylbenzene in its upper part, and separated the heavy alkylate in its bottom. The mono-alkylbenzene obtained from the upper part of the third column, which showed traces of heavy alkylate, was fed to the purification bed, responsible for eliminating the chromophore precursors. Once purification took place, the effluent was fed to the fourth distillation column. This column separated light by-products formed during the purification step, (mainly benzene, generated through transalkylation reactions at ppm levels) in its upper part, while the compounds found in the bottom were highly pure mono-alkylbenzenes. Said highly pure mono-alkylbenzenes were later sulphonated in a mono-tubular, falling film reactor, being the sulphonation agent $SO_3$ dissolved in nitrogen, and, to complete the reaction, these mono-alkylbenzenes were matured and hydrolyzed.

As stated in the previous paragraph, the purification step was carried out by treating the mono-alkylbenzene (obtained from fractioning raw alkylate) in a fixed bed purifier (reactor), where a certain amount of commercial acid clay was placed. In this example, the clay used was characterized by a silica-alumina weight rate of 4.9:1.0, partly neutralized by 1.4 wt % of $K_2O$, and 1.2 wt % of MgO, and also characterized by 2.9 wt % of $Fe_2O_3$, and 0.5 wt % of $TiO_2$. This clay was previously activated by sending a hot, inert gas flow to eliminate the adsorbed water. Activation and operation conditions are summarized in table 19.

TABLE 19

| | |
|---|---|
| Purified Temperature (° C.) | 110 |
| LHSV ($h^{-1}$) Purification | 3 |
| Activation Temperature (° C.) | 120 |
| LHSV ($h^{-1}$) Activation | 2 |
| Activation Period (h) | 12 |
| Activation Gas | $N_2$ |

Conditions for the sulphonation of purified and non-purified mono-alkylbenzenes obtained by combination of catalysts A-C and B-C are summarized in table 20:

TABLE 20

| | |
|---|---|
| SO3/LAB Molar Ratio | 1.10:1 |
| Reaction Time | 1.5 hours |
| Reaction Temperature | 40-45° C. |
| Digestion Time | 1 hour |
| Digestion Temperature | 40-45° C. |
| Hydrolysis Time | 0.5 hours |
| Hydrolysis Temperature | 40-45° C. |

Final sulphonation color of the linear alkylbenzene sulphonates (LAS) obtained (called LAS A-C if mono-alkylbenzene comes from alkylation with the combination of catalysts A-C, and LAS B-C if mono-alkylbenzene comes from alkylation with the combination catalysts B-C) was analyzed by using the Klett-Summerson colorimeter. In order to evaluate the effect of the purification step on the sulphonation final color when using catalysts A and B, the mono-alkylbenzene was also sulphonated under the same conditions, without the purification step with clay. Sulphonation color of sulphonated, non-purified mono-alkylbenzene (LAS from non-purified mono-alkylbenzene) and sulphonation color of sulphonated, purified mono-alkylbenzene (LAS from purified mono-alkylbenzene) in alkylates obtained by the combination of catalysts A-C and B-C is summarized in table 21:

TABLE 21

| Sulphonate | Sulphonation Color (Klett-Summerson Scale) | |
|---|---|---|
| | LAS A-C | LAS B-C |
| Non-purified, Mono-alkylbenzene LAS | 23 | 19 |
| Purified, Mono-alkylbenzene LAS | <7 | <7 |

As table 21 shows, purification of mono-alkylbenzene by using acid clay allows a significant reduction in the sulphonation color of the LAS from the purified mono-alkylbenzene alkylate in comparison to the LAS from the non-purified mono-alkylbenzene (at least 70-80% lower, sulphonation color below 7 can not be measured by the Klett-Sumerson scale). Note that the LAS sample from non-purified mono-alkylbenzene derived from a combination of catalysts B-C shows a sulphonation color significantly lower (17% lower) than the color obtained by the combination of catalysts A-C. This implies that, during the alkylation step, catalyst B produces a smaller quantity of chromophore precursors than catalyst A does. By reducing the sulphonation color, the quality of the neutralized final product is increased, especially when the final product is used in liquid detergent formulae, since this color may interfere in the visual effect of coloring matter added to the detergent formula.

Example 7

This example shows the advantages of adding the hydrotropic precursor (obtained according to what was described in example 1), to the mono-alkylbenzene (obtained by fractionation of raw alkylate) before the step of purification of said alkylbenzene (commented on example 6), after which the resulting alkylate is separated and sulphonated. The hydrotrope as such is formed by sulphonating (and later neutralizing) the hydrotropic precursor in the sulphonation step, either isolated or mixed with the linear mono-alkylbenzene. Besides, it is compared the hydrotropic effect in the LAS obtained by combination of A-C and B-C catalysts.

The effluents (raw alkylate) of the beds 1 and 2 (using A-C and B-C in different operations, in a way analogous to example 5) were mixed, and later distilled in a manner equivalent to that indicated in examples 5 and 6, to isolate the mono-alkylbenzenes. To these mono-alkylbenzenes the hydrotropic precursor was added, after that the resulting mixture was purified with acid clay under the same conditions as those indicated in example 6, and the resulting effluents were distilled to separate the light by-products of the final alkylate. Once said alkylates have been sulphonated, they were finally neutralized with aqueous sodium hydroxide in an stoichiometric quantity.

In order to evaluate the hydrotropic effect according to the context of the 2-phenyl isomer, there were produced six samples of mono-alkybenzene purified with different contents of 2-phenyl isomer in the alkylation step (as defined in the example 5) for each combination of catalysts indicated in the examples 3 and 4 (A-C) and (B-C). The samples are called S1 (A-C and B-C), S2 (A-C and B-C) and S3 (A-C and B-C) according to its content of 2-phenyl isomers and their origin. The flows were adjusted when operating the configurations A-C and B-C to obtain the same context of 2-phenyl isomers. The blank tests (without adding hydrotrope) and the tests with sodium xylene Sulphonate (SXS) were carried out with alkylate derived from the A-C and B-C systems with the same 2-phenyl isomer content as the S1, S2 and S3 indicated before, so that the same notation is used to distinguish the 2-phenyl isomer content:

TABLE 22

| | S1 (A-C and B-C) | S2 (A-C and B-C) | S3 (A-C and B-C) |
|---|---|---|---|
| 2-phenyl isomers (wt %) | 18.8 | 58.1 | 70.0 |

The solubilizing effect of the hydrotrope has been evaluated in terms of the Cooled Cloud Point (CCP) of the final sulphonated and neutralized product. Said product was diluted with water until obtaining typical commercial concentrations (20, 25, 30% by weight in water). To see the effect of the hydrotropic precursor, samples of 90 wt % of the mono-alkylbenzene and 10% of this hydrotropic precursor were prepared. Besides, blank samples were prepared, that is, without adding hydrotropic precursor. Thus, samples were prepared with 100% of the product derived from the A-B system and samples with 100% of the by-product of the aforementioned B-C system, with the same 2-phenyl isomer content as the samples to which the hydrotropic precursor had been added. Another well-known hydrotrope, sodium xylene sulphonate (SXS), was added to samples without hydrotropic precursor (90% pure sodium sulphonate alkybenzene with 2-phenyl isomer content equivalent to those of the other essays and 10% SXS), and after that it was diluted with water until the same commercial concentrations of the previous samples. The results are summarized in table 23:

TABLE 23

| | | Active material in Cleaning composition [% weight in water] | | |
|---|---|---|---|---|
| | | 20% | 25% | 30% |
| | | Cooled Cloud Point, ° C. | | |
| Alkylate from the A-C System | 100% S1 (A-C) | 8 | 16 | 24 |
| | 90% S1 (A-C) + 10% SXS (sodium xylene sulphonate) | 7 | 14 | 20 |
| | 90% S1 (A-C) + 10% Hydrotropic precursor | 1 | 7 | 14 |
| | 100% S2 (A-C) | 17 | 20 | (*) |
| | 90% S2 (A-C) + 10% SXS (sodium xylene sulphonate) | 14 | 17 | (*) |
| | 90% S2 (A-C) + 10% Hydrotropic precursor | 13 | 16 | 20 |
| | 100% S3 (A-C) | 16 | 20 | 24 |
| | 90% S3 (A-C) + 10% SXS (sodium xylene sulphonate) | 12 | 15 | 17 |
| | 90% S3 (A-C) + 10% Hydrotropic precursor | 7 | 9 | 13 |
| Alkylate from the B-C System | 100% S1 (B-C) | 9 | 17 | 24 |
| | 90% S1 (B-C) + 10% SXS (sodium xylene sulphonate) | 7 | 15 | 20 |
| | 90% S1 (B-C) + 10% Hydrotropic precursor | 1 | 7 | 14 |
| | 100% S2 (B-C) | 18 | 20 | (*) |
| | 90% S2 (B-C) + 10% SXS (sodium xylene sulphonate) | 14 | 17 | (*) |
| | 90% S2 (B-C) + 10% Hydrotropic precursor | 13 | 16 | 20 |
| | 100% S3 (B-C) | 16 | 20 | 24 |
| | 90% S3 (B-C) + 10% SXS (sodium xylene sulphonate) | 12 | 15 | 17 |
| | 90% S3 (B-C) + 10% Hydrotropic precursor | 7 | 9 | 13 |

(*) Turbid at room temperature (T = 25° C.)

From table 23 two fundamental conclusions can be extracted. First, it can be seen how for the samples with low 2-phenyl content and without hydrotrope (samples 100% S1 and 100% S2), the Cooled Cloud temperatures derived from the alkylate from A-C system are slightly higher than those of the B-C system, although the addition of hydrotropes tends to lower those cloud points up to equivalent levels (and at high concentrations of 2-phenyl isomers, this difference disappears). This fact seems to be related to the higher content of branched mono-alkylates sulphonate (more soluble than the linear equivalents) of A-B system. The second conclusion refers to the fact that the ability of the hydrotrope contemplated in this patent to reduce the cooled cloud temperature is much higher than that of SXS, especially for samples with very low (18%) or very high (70%) 2-phenyl isomer content, both for both products of the A-C catalytic system and for those of the B-C system. Therefore, it can be concluded that the product of the B-C system is practically as soluble as that of the A-B system (in fact, equal to high concentrations of 2-phenyl isomers), and that the addition of the hydrotrope contemplated in this patent reduces the CCP of the by-product of the catalytic A-B and B-C systems up to equivalent levels, and much lower that those obtained when using a commercial hydrotrope such as SXS.

Example 8

This example illustrates the advantages of the catalyst based on a zeolite Y containing high loads of rare earth metals and sodium (catalyst B in example 2) in relation to the use of the catalyst based on a zeolite Y containing low loads of rare earth metals and sodium (catalyst A in example 2), when carrying out the alkylation of benzene with long-chain linear alpha-olefins ($C_{20}$-$C_{22}$ range), comparing with the results obtained when HF is used, a catalyst used at length at industrial scale for this same process.

The benzene was dried with a molecular sieve in order to minimize the water addition, and then it was mixed with a mixture of long-chain linear alpha-olefins. The alkylation tests in pilot plant, in the case of the solid catalyst, were carried out in a thin bed isothermal reactor, with 24-hour reactor cycles, followed by cycles of benzene wash during the same period. A standard cycle comprises a 24-hour reaction cycle, with a benzene-olefin molar ratio of 50:1, followed by a benzene wash cycle during the same period of time. The operation conditions are summarized in table 24:

TABLE 24

| Catalyst | A |
|---|---|
| Particle diameter (mm × mm) | 0.50-1.25 |
| Catalyst volume (cm³) | 122 |
| Reaction temperature (° C.) | 140-150 |
| Regeneration temperature (° C.) | 260 |
| Reaction pressure. (kgf/cm²) | 20 |
| Regeneration pressure (kgf/cm²) | 40 |
| LHSV reaction (h⁻¹) | 4-8 |
| LHSV regeneration (h⁻¹) | 1 |
| Reaction time (h) | 24 |
| Regeneration time (h) | 24 |
| Benzene/olefin molar ratio | 50 |

The mixture of alpha-olefins used as feed composition is summarized below in table 25:

TABLE 25

| Compound | (wt %) |
|---|---|
| <$C_{20}$olefin | 0.1 |
| $C_{20}$olefin | 43.7 |
| $C_{22}$olefin | 35.3 |
| $C_{24}$olefin | 19.1 |
| >$C_{40}$olefin | 0.7 |

Twelve alkylation reaction cycles were carried out using the zeolites Y A and B of example 2. The three first cycles were carried out with an LHSV of 8 h⁻¹, at T=150° C. (cycle 1). Then, three cycles at 6 h⁻¹ y T=150° C. (cycle 2). The last four cycles were carried out with an LHSV of 8 h⁻¹, two of them at T=150° C. and the last two at a lower temperature, T=140° C. (cycle 3). All these cycles were carried out in order to analyze the effect of the temperature and the spatial speed on the catalyst yield. The products were analyzed by Gas Chromatography (GC) and Flame Ionization Detector (FID).

The alkylation with HF was carried out discontinuously on a cooled reactor with continuous agitation, since the alkylation is an exothermal reaction and it is necessary to extract heat from the reactor to maintain the desired reaction temperature constant, being typical of the state-of-the-art. In the reactor it is injected a certain amount of the previously considered mixture of linear alpha-olefins (composition as reflected in table 25) mixed with dry benzene until obtaining the desired benzene-olefin molar ratio. This mixture of benzene and olefins was previously heated to the reaction temperature selected. Then, a certain volume of liquid HF was injected to the reactor until reaching the selected HF-olefin volume ratio. The reaction time was adjusted to 10 minutes, in order to obtain an LHSV=6 h⁻¹, typical of the state-of-the-art of alkylation with HF. The conditions of operation of the alkylation reaction with HF are summarized in table 26:

TABLE 26

| | Catalyst HF |
|---|---|
| Reaction temperature (° C.) | 60 |
| Reaction time (min) | 10 |
| HF/Olefin volume ratio | 1 |
| Benzene/olefin molar ratio | 10 |

The results compiled in table 27 correspond to the average product distribution (monoalkylbenzenes and byproducts, including light by-products and heavy by-products, once the benzene without reaction has been separated) of those cycles used by solid catalysts A and B with different LHSV and temperature conditions (called cycles 1, 2 and 3). The results corresponding to the HF technology are included in the lower part of table 22 to compare the yields of HF and solid catalyst.

TABLE 27

| Catalyst | Cycle | LHSV (h⁻¹) | T (° C.) | Conversion (%) | Mono-Alkylbenzene (% weight) | Total by-products (% weight) |
|---|---|---|---|---|---|---|
| A | 1 | 8 | 150 | 99.7 | 99.6 | 0.37 |
|   | 2 | 4 | 150 | 99.9 | 99.8 | 0.23 |
|   | 3 | 4 | 140 | 99.8 | 99.7 | 0.26 |

TABLE 27-continued

| Catalyst | Cycle | LHSV (h⁻¹) | T (° C.) | Conversion (%) | Mono-Alkybenzene (% weight) | Total by-products (% weight) |
|---|---|---|---|---|---|---|
| B | 1 | 8 | 150 | 99.8 | 99.7 | 0.29 |
|   | 2 | 4 | 150 | 99.9 | 99.8 | 0.23 |
|   | 3 | 4 | 140 | 99.8 | 99.7 | 0.25 |
| HF | — | 6 | 60 | 99.9 | 99.7 | 0.30 |

As it can be seen in table 27, the activity of zeolite Y having rare earth metals A and B as additives is very similar (slightly higher for the B catalyst), since the olefin conversion is always over 99.7%. When the by-products generated are analyzed, both the catalysts A and B as HF present high selectivity as regards minimizing the light by-products and heavy alkylate. The quantity of total by-products generated by the solid catalysts A and B are below 0.4 wt % in the three cycles evaluated, and in cycles 2 and 3 is even better when HF is used. Therefore, both catalysts based on zeolites Y with rare earths (A and B) are equivalent, in terms of conversation and selectivity towards monoalkylbenzenes, to the catalyst used at industrial level (HF).

The distribution of isomers corresponding to the previous experiments is summarized in table 28. As in table 27, the result line of the lower part corresponds to the results associated to the reaction with HF, under conditions of operation as previously defined in table 26.

TABLE 28

| Catalyst | Cycle | Branched alkylate (% weight) | 2-phenyl (% weight) | 3-Phenyl (% weight) | 4,5,6,7-phenyl (% weight) |
|---|---|---|---|---|---|
| A | 1 | 16.8 | 17.6 | 14.0 | 51.6 |
|   | 2 | 18.7 | 17.0 | 13.4 | 51.0 |
|   | 3 | 16.4 | 17.7 | 14.4 | 51.8 |
| B | 1 | 12.6 | 17.4 | 14.2 | 55.8 |
|   | 2 | 14.0 | 18.3 | 13.5 | 54.2 |
|   | 3 | 12.3 | 16.9 | 14.6 | 56.2 |
| HF | — | 12.4 | 19.9 | 12.1 | 55.8 |

In table 28, the isomer distribution is similar when compared to the products of zeolites Y (A and B) with those of HF. The main difference is related to the branched alkylate content. As it can be seen, the quantity of branched alkylate generated when zeolite is used with low loads (7%) of rare earth metals is approximately a 27% higher than the quantity generated when HF is used as a catalyst. However, the quantity of branched alkylate produced by the catalyst B is equivalent, and even lower (cycle 3) than that produced by HF. Therefore, from this point of view, the catalyst B is capable of producing less branched alkylate than the catalyst A (25% less), and approximately the same amount that the homogeneous catalyst used at industrial level (HF). With respect to the 2-phenyl isomer content, it can be seen that the HF technology produces a slightly smaller amount of 2-phenyl isomers than the zeolites Y modified with rare earths (A and B).

Therefore, it is observed that the catalyst B is a catalyst equivalent to HF in the process of benzene alkylation with pure alpha-olefins (in terms of conversion, selectivity to monoalkylate and alkylates), and besides the complex handling of an acid as corrosive as HF is avoided. Moreover, the catalyst B improves the behavior of the catalyst A in this process by considerably lowering (25%) the production of branched alkylates.

The invention claimed is:

1. Procedure for obtaining a linear monoalkylaromatic compound with a 2-phenyl isomer content able to be adjusted between 18% and 70 wt %, through the catalytic alkylation of an aromatic compound with a purified alkylating agent, comprising the following steps:
   i) catalytically dehydrogenating a linear paraffin feed,
   ii) selectively dehydrogenating the diolefins produced as a by-product of step i) to mono-olefins, to obtain the raw alkylating agent,
   iii) purifying the raw alkylating agent obtained in step ii), separating the non-linear products contained in the effluent of step ii), to obtain the purified alkylating agent,
   iv) treating the non-linear products extracted in step iii) to generate the hydrotropic precursor,
   v) alkylating the aromatic hydrocarbon with the mono-olefins present in the purified alkylating agent, through the combination of the following processes,
      a) an alkylation process with a catalyst that produces a linear alkylaromatic compound with a maximum content of 2-phenyl isomers of 20 wt %
      b) an alkylation process with a catalyst that produces a linear alkylaromatic compound with a minimum content of 2-phenyl isomers of 20 wt % comprising a MOR-type zeolite, between 0.01%-0.20 wt % of at least one of the metals selected from the group consisting of: Li, Na, K, Mg, and Ca with a maximum of 0.01% Na, and between 0-0.5 wt % of at least one of the metals selected from the group consisting of Ti, Zr, and Hf
   vi) fractionating the effluent of step v) to separate the aromatic compounds which have not reacted, the paraffins and the lightest and heaviest by-products, from the linear mono-alkylaromatic compounds of interest
   vii) purifying the fraction of linear mono-alkylaromatic compounds coming from step vi), wherein the catalyst producing a maximum of 20 wt % of 2-phenyl isomers comprises a FAU-type zeolite, between 0.5-2.0 wt % of at least one of the metals selected from the group consisting of: Li, Na, K, Mg, and Ca, and rare earth metals in between 4.5-10 wt % of La, between 1.2-4 wt % of Ce, between 0.5-1.5 wt % of Pr, and between 2-3 wt % of Nd.

2. Procedure for obtaining a linear monoalkylaromatic compound according to claim 1, where the catalyst producing a maximum of 20% of 2-phenyl isomers comprises an amount of 0.9 wt % of Na.

3. Procedure for obtaining a linear monoalkylaromatic compound according to claim 1, where the catalyst producing a maximum of 20% of 2-phenyl isomers comprises:
   a) a x-ray powder diffraction pattern characterized in that the most intense diffraction peak appears in the 2-theta angle corresponding to 6.2°, and the rest of the main peaks appear in 2-theta diffraction angles corresponding to 23.6°, 20.3°, 21.6°, 27.0°, 31.3°, ordered from highest to lowest intensity of the associated peaks,
   b) a silicon/aluminum total molar rate between 0.5:1.0 and 3.0:1.0
   c) a structure network silicon/aluminum molar rate between 1.5:1.0 and 2.5:1.0
   d) a total specific area (BET) between 500-1000 m²/g,
   e) a micropore area between 500-900 m²/g,
   f) a micropore specific volume between 0.1-0.3 ml/g,
   g) a macropore distribution where the macropore diameter is within the range of 20-2000 ten thousand micro-meter range.

4. Procedure for obtaining a linear monoalkylaromatic compound according to claim 1, where the paraffins used comprise between 8-30 carbon atoms.

5. Procedure for obtaining a linear monoalkylaromatic compound according to claim 1, where the aromatic hydrocarbon is selected from a group consisting of:
benzene, toluene, xylene or mixtures thereof.

6. Procedure for obtaining a linear monoalkylaromatic compound according to claim 1, where the aromatic hydrocarbon and the purified alkylating agent are mixed before the reaction to alkylation of step v) in an aromatic hydrocarbon:olefin molar rate between 5:1-70:1.

7. Procedure for obtaining a linear monoalkylaromatic compound according to claim 1, where the mixture of aromatic hydrocarbon and the purified alkylating agent comprises a maximum of 0.3 wt % of non-linear compounds other than the aromatic hydrocarbon.

8. Procedure for obtaining a linear monoalkylaromatic compound according to claim 1, where the mixture of aromatic hydrocarbon and the purified alkylating agent comprises between 0-0.1 wt % of water.

9. Procedure for obtaining a linear monoalkylaromatic compound according to claim 1, where the alkylation reactions of step v) are carried out simultaneously.

10. Procedure for obtaining a linear monoalkylaromatic compound according to claim 1, where the catalyst used in the alkylation reaction is in the reactor in an arrangement selected from the group consisting of: a fixed bed with a sole catalyst, a fixed bed with two different catalysts completely mixed, at least two different fixed beds with the same catalyst each, at least two different fixed beds with a different catalyst each, a fluidized bed with one or more different catalysts, a slurry reactor with one or more different catalysts.

11. Procedure for obtaining a linear monoalkylaromatic compound according to claim 1, where the alkylation process is carried out in one configuration of reactors comprising at least one of the reactor configurations selected from the group consisting of: an independent reactor, at least two parallel reactors, at least two serial reactors and combinations of said configurations.

12. Procedure for obtaining a linear monoalkylaromatic compound according to claim 1, where the purification step of step vii) is carried out through selective absorption and/or hydrogenation and/or fractioning.

13. Procedure for obtaining a linear monoalkylaromatic compound according to claim 12, where the selective adsorption is carried out through a selective clay-type adsorbent.

14. Procedure for obtaining a linear monoalkylaromatic compound according to claim 13, where the clay comprises:
a) a silicone:aluminum total molar rate between 3:1-5:1
b) between 1-4 wt % $Fe_2O_3$
c) between 0.5-2.0 wt % $K_2O$
d) between 0.2-2.0 wt % $MgO$
e) between 0.1-1.0 wt % $TiO_2$
f) between 1800 y 2500 ppm Na
g) a specific area expressed as a BET area comprised between 150-500 $m^2/g$
h) a cumulative pore volume between 0.1-2 ml/g
i) a macropore distribution where the macropore diameter is within the range of 20-800 ten thousand micro-meters.

15. Procedure for obtaining a linear monoalkylaromatic compound according to claim 1, where the olefins of step v) are linear α-olefins.

16. Procedure for obtaining a linear monoalkylaromatic compound according to claim 15, where the α-olefins of step v) comprise between 9-30 carbon atoms.

17. Procedure for obtaining a linear monoalkylaromatic compound according to claim 1, where the reaction temperature is comprised between 20-400° C.

18. Procedure for obtaining a linear monoalkylaromatic compound according to claim 1, where the spatial speed is 1-15 $hr^{-1}$.

19. Procedure for obtaining a linear monoalkylaromatic compound according to claim 1, comprising a step viii) of sulphonation and neutralization of the compound obtained in step vii).

20. Procedure for obtaining a linear monoalkylaromatic compound according to claim 1, where steps i), ii), iii) and iv) are optional.

21. Procedure for obtaining a linear monoalkylaromatic compound according to claim 19, wherein said neutralization in step viii) is carried out in the presence of an alkaline substance comprising one or more cations selected from Na, K, $NH_4^+$, Mg, Ca, Ba, or substituted ammonium alkali.

* * * * *

UNITED STATES PATENT AND TRADEMARK OFFICE
CERTIFICATE OF CORRECTION

PATENT NO. : 8,237,001 B2
APPLICATION NO. : 12/746485
DATED : August 7, 2012
INVENTOR(S) : Berna Tejero et al.

It is certified that error appears in the above-identified patent and that said Letters Patent is hereby corrected as shown below:

In the Specifications:

Col. 6, line 16: "comprises a MOR typezeolite, between" should read --comprises a MOR type zeolite, between--

Col. 8, line 4: "to 30% by weight" should read --15 to 30% by weight--

Col. 8, line 27: "clay typeadsorbent, which comprises:" should read --clay type adsorbent, which comprises:--

Col. 12, line 25: "Flow 20 is is mixed with" should read --Flow 20 is mixed with--

Col. 16, line 43: "third column is separated the" should read --third column separated the--

Signed and Sealed this
Fourteenth Day of May, 2013

Teresa Stanek Rea
*Acting Director of the United States Patent and Trademark Office*